(12) United States Patent
Shiono et al.

(10) Patent No.: US 6,207,365 B1
(45) Date of Patent: Mar. 27, 2001

(54) FLUORESCENT ENZYME SUBSTRATES AND METHOD FOR DETERMINING ENZYME ACTIVITIES

(75) Inventors: Hirofumi Shiono; Hitoshi Nohta; Chika Utsuyama, all of Shizuoka (JP)

(73) Assignee: Laboratory of Molecular BioPhotonics, Shizuoka (JP)

( * ) Notice: Subject to any disclaimer, the term of this patent is extended or adjusted under 35 U.S.C. 154(b) by 0 days.

(21) Appl. No.: 09/125,288

(22) PCT Filed: Dec. 16, 1997

(86) PCT No.: PCT/JP97/04631

§ 371 Date: Aug. 14, 1998

§ 102(e) Date: Aug. 14, 1998

(87) PCT Pub. No.: WO98/27224

PCT Pub. Date: Jun. 25, 1998

(30) Foreign Application Priority Data

Dec. 16, 1996 (JP) ..................................... 8-335956

(51) Int. Cl.[7] .............................. C12Q 1/00; C12Q 1/44; C07D 319/12; C07D 319/14
(52) U.S. Cl. .................................. 435/4; 435/19; 435/21; 549/283; 549/362
(58) Field of Search ................................... 549/283, 362; 536/4.1; 435/4, 14, 19, 21; 514/457

(56) References Cited

U.S. PATENT DOCUMENTS

| | | | |
|---|---|---|---|
| 5,316,906 | 5/1994 | Haughland et al. | 435/4 |
| 5,443,986 * | 8/1995 | Haughland et al. | 435/4 |
| 5,576,424 * | 11/1996 | Mao et al. | 536/17.9 |
| 5,830,912 * | 11/1998 | Gee et al. | 514/457 |

OTHER PUBLICATIONS

Gallagher et al. The Development of Two Fluorimetric Assays for the Determination of Pyroglutamyl Aminopeptidase Type–II Activity. Anal. Biochem. 250, pp. 1–9. (1997) No month found.*
Berkenkamp, B.; "Effect of Coumarin on some Pathogens of Sweetclover", Can. J. Plant Sci. 51: 299–303, Jul. 1971.
Schön, Walter J.; "Zur Bildung der beiden stereoisomeron o–Oxyzimtsäureglucoside und ihre Trennung durch Gelfiltration", Angewandte Botanik, vol. 47, No. 5–6, 1973, pp. 257–264. No month found.
Riviere, J. et al.; "Libération de la coumarine par les microorganismes du sol", Annales de L'Institut Pasteur, vol. 113, No. 1, 1967, pp. 109–116. No month found.
Huisman, O.C., et al.; "Conversion of o–(β–D–Glucosyloxy)–Hydrocinnamic Acid in *Melilotus alba*", Phytochemistry, vol. 9, No. 1, 1970, pp. 131–137. No month found.

Poulton, J.E., et al.; "Intracellular Localization of Two Enzymes Involved in Coumarin Biosynthesis in *Melilotus alba*", Plant Physiology, vol. 65, No. 2, Feb. 1980, pp. 171–175.
Schroeder, C., et al.; "Preparative Biosynthesis of Natural Glucosides and Fluorogenic Substrates for β–Glucosidases followed by in vivo C NMR with High Density Plant Cell Cultures", Tetrahedron, vol. 52, No. 3, Jan. 15, 1996, pp. 925–934.
Gallagher et al., "The Development of Two Fluorimetric Assays for the Determination of Pyroglutamyl Aminopeptidase Type–II Activity", Analytical Biochemistry 250, (Jul. 1997), Article No. AB972195, pp. 1–9.
Smali et al., "An Improved Synthesis of 3–Methylcoumarins & their Linear & Angular Benzo Derivatives", Indian Journal of Chemistry, vol. 22B, Apr. 1983, pp. 352–354.
Feigenbaum et al., "Simplified Method for the Preparation of Aromatic Sulfuric Acid Esters", Chem. Depart. of the Cancer Research Institute of the Univ. of Jerusalem, and the Depart. of Chemistry, NYU, vol. 63, 1941, pp. 3529–3530.
Porter et al. Photoregulation of Enzymes, Chapter 4 of "Biological Applications of Photochemical Switches", Biorganic Chemistry Series, vol. 2. John Wiley & Sons, Inc., New York. (1993) pp. 197–241.
W. W. Prichard, "Hydroquinone Diacetate", Organic Synthesis, Collective vol. III, (1955), pp. 452–453.
Isadore B. Berlman, "Handbook of Fluorescence Spectra of Aromatic Molecules", Second Edition, Academic Press, 1971, p. 330.
Nakazono et al., "Chemiluminescent Assays for β–D–Galactosidase and Alkaline Phosphatase Using Novel Luminol Derivatives as Substrates", Anal. Sciences, Dec. 1992, vol. 8, pp. 779–783.
Morozowich et al., "Synthesis and Bioactivity of Lincomycin–2–Phosphate", Jour. of Pharmaceutical Sciences, vol. 58, No. 12, Dec. 1969, pp. 1485–1489.
Wittig et al., Organic Synthesis, Collective vol. V, (1973), pp. 751–754.

\* cited by examiner

*Primary Examiner*—Ralph Gitomer
*Assistant Examiner*—Marjorie A. Moran
(74) *Attorney, Agent, or Firm*—Leydig, Voit & Mayer, Ltd.

(57) ABSTRACT

The enzyme substrate according to this invention has within its molecule both a group to be cleaved by an enzyme reaction and a group that forms a strongly fluorescent coumarin derivative through intramolecular lactonization when cleaved by the enzyme reaction. Furthermore, the method for determining an enzyme activity according to this invention comprises conducting the enzyme reaction by the use of the enzyme substrate of the invention and determining the enzyme activity by means of the measurement of fluorescence of the coumarin derivative formed.

21 Claims, 11 Drawing Sheets

FLUORESCENT ENZYME SUBSTRATES AND METHOD FOR DETERMINING ENZYME ACTIVITIES

TECHNICAL FIELD

This invention relates to a novel fluorescent enzyme substrate and a method for determining an enzyme activity by means of the enzyme substrate.

BACKGROUND ART

Techniques are known to determine the activity of a specified enzyme with high sensitivity by measuring its fluorescence. Among the techniques, there is a method known where a 4-methylumbelliferone derivative is employed as a substrate (see, the scheme below). Since the enzyme reaction product (4-methylumbelliferone) from the substrate is a phenol derivative in this method, the enzyme activity in the reaction is inhibited by a phenolate ion that has increased in the reaction solution. Thus, there is the possibility that it will become difficult to determine the enzyme activity consistently within a sufficient period of reaction time.

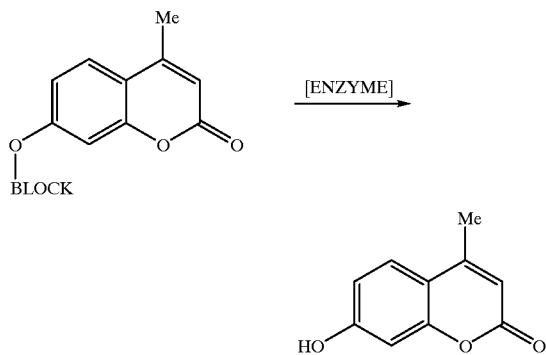

Also, U.S. Pat. Nos. 5,316,906 and 5,443,986 disclose an enzyme reaction substrate having a certain substituent that is released by an enzyme reaction and emits strong fluorescence as well as a method for determining an enzyme activity by means of the substrate. In this case, the substrate has weak fluorescence even before the enzyme reaction takes place and further, it generates a precipitate after the enzyme reaction (see, the scheme below).

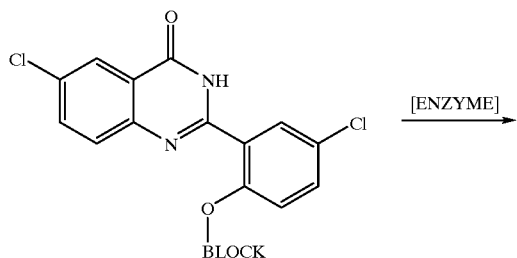

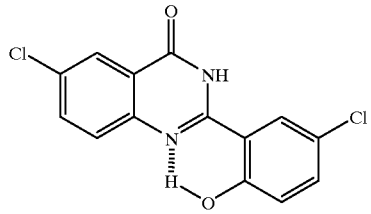

DISCLOSURE OF THE INVENTION

The present inventors have developed novel enzyme substrates and methods for determining enzyme activities, and have discovered novel fluorescent enzyme substrates characterized by the following: (1) they do not display any fluorescence before enzyme reactions, but their reaction products display strong fluorescence after the reactions; and (2) the enzyme reaction products have chemically inert structures (aromatic compounds) that are not phenol derivatives. Furthermore, the present inventors have succeeded in establishing methods for determining enzyme activities by means of such enzyme substrates and accomplished this invention. The scheme as shown below illustrates the concept of the invention.

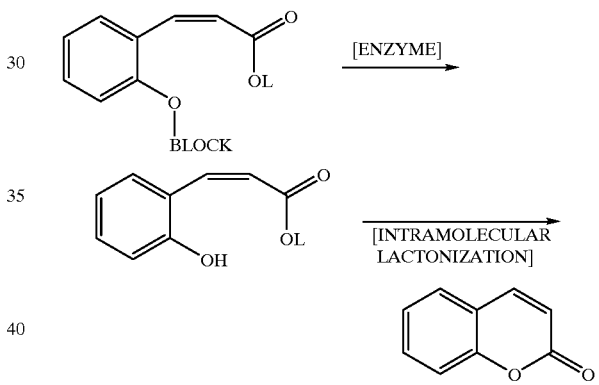

Namely, the novel enzyme substrates according to this invention yield products having coumarin skeletons (coumarin derivatives) that display strong fluorescence after the enzyme reactions; therefore, they are not provided with functional groups such as phenolic hydroxyl and are biochemically inert, also being not susceptible to aqueous solutions having a wide range of pH.

Furthermore, the methods for determining enzyme activities according to this invention determine the enzyme activities with high sensitivity by employing the above-mentioned substrates through fluorescence measurement.

Specifically, this invention, in a general sense, provides an enzyme substrate represented by the following formula:

(BLOCK-O)-X

wherein BLOCK (or BLOCK group) is any one blocking group selected from the group consisting of: a monovalent blocking group derivable by removal of one hydroxyl from a phosphoric acid group, a sulfuric acid group, or a salt biologically exchangeable with the foregoing groups; a monovalent blocking group derivable by removal of a hydroxyl from an aliphatic carboxyl, an aromatic carboxyl, an amino acid carboxyl, or a peptide carboxyl; and a monovalent blocking group derivable by removal of any one hydroxyl from a monosaccharide or a polysaccharide, and said BLOCK is cleaved from said substrate by the action of a specified enzyme to yield a HO—$X_{cu}$ product, and further, said HO—$X_{cu}$ product intramolecularly forms a lactone ring to provide a coumarin derivative;

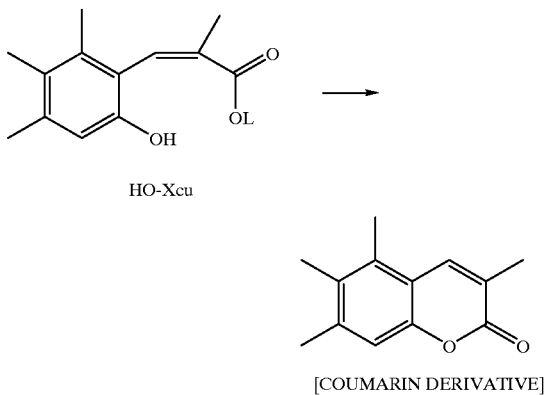

HO-Xcu

[COUMARIN DERIVATIVE]

wherein $X_{cu}$ has a structure represented by the following formula and is covalently bound to oxygen O at $C_1$ carbon,

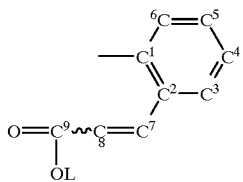

wherein L represents H, $NH_4$, alkyl having 1 to 4 carbons, tetraalkylammonium having 1 to 4 carbons, or an alkaline metal or an alkaline earth metal; and further, wherein the coumarin derivative has a structure represented by the following formula:

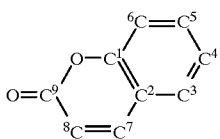

Moreover, the invention provides the above-mentioned enzyme substrate wherein the $C^3$–$C^4$ bond forms a 5- or 6-membered aromatic ring; H is bound to $C^5$, $C^6$, and $C^7$; and H or $CH_3$ is bound to $C^8$.

Also, the invention provides the above-mentioned enzyme substrate wherein the $X_{cu}$ has a structure represented by the following formula:

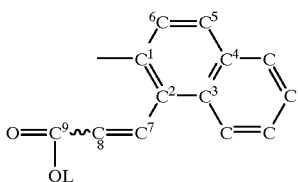

Also, the invention provides the above-mentioned enzyme substrate wherein dialkylamino having 1 to 3 carbons is bound to $C^5$; hydrogen is bound to $C^3$, $C^4$, $C^6$, and $C^7$; and H or $CH_3$ is bound to $C^8$.

Furthermore, the invention provides the above-mentioned enzyme substrate wherein the $X_{cu}$ has a structure represented by the following formula:

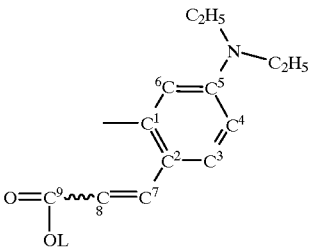

Still further, the invention provides the above-mentioned enzyme substrate wherein alkyloxy having 1 to 3 carbons is bound to $C^3$ and $C^5$; H is bound to $C^4$, $C^6$, and $C^7$; and H or $CH_3$ is bound to $C^8$.

Also, the invention provides the above-mentioned enzyme substrate wherein the $X_{cu}$ has a structure represented by the following formula:

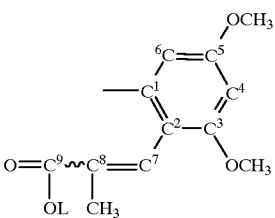

In addition, the invention provides the above-mentioned enzyme substrate wherein the BLOCK is a phosphoric acid group ($PO_3^{-2}$), D-galactopyranoside, or acetyl ($CH_3CO$).

Moreover, the invention provides a method for determining an enzyme activity, said method comprising the following two steps ((A) and (B)) of:

(A) treating a sample containing an enzyme to be detected, with an enzyme substrate represented by the following formula:

(BLOCK-O)-$X_{cu}$ 

wherein BLOCK is any one blocking group selected from the group consisting of: a monovalent blocking group derivable by removal of one hydroxyl from a phosphoric acid group, a sulfuric acid group, or a salt biologically exchangeable with the foregoing groups; a monovalent blocking group derivable by removal of a hydroxyl from an aliphatic carboxyl, an aromatic carboxyl, an amino acid carboxyl, or a peptide carboxyl; and a monovalent blocking group derivable by removal of any one hydroxyl from a monosaccharide or a polysaccharide, and said BLOCK is cleaved from said substrate by the action of a specified enzyme to yield a HO—$X_{cu}$ product, and further, said HO—$X_{cu}$ product intramolecularly forms a lactone ring to provide a coumarin derivative;

wherein $X_{cu}$ has a structure represented by the following formula, the $C^7$–$C^2$ bond and the $C^8$–$C^9$ bond have cis-configuration with respect to the $C^7$=$C^8$ double bond, and the $X_{cu}$ is covalently bound to oxygen O at $C^1$ carbon,

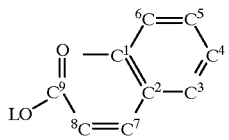

wherein L represents H, NH$_4$, alkyl having 1 to 4 carbons, tetralkylammonium having 1 to 4 carbons, or an alkaline metal or an alkaline earth metal; and further, wherein said coumarin derivative has a structure represented by the following formula:

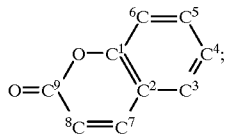

and (B) detecting said coumarin derivative.

Also, the invention provides a method for determining an enzyme activity, said method comprising the following two steps ((A) and (B)) of:

(A) treating a sample containing an enzyme to be detected, under irradiation conditions, with an enzyme substrate represented by the following formula:

(BLOCK-O)-X$_{cu}$ wherein BLOCK is any one blocking group selected from the group consisting of: a monovalent blocking group derivable by removal of one hydroxyl from a phosphoric acid group, a sulfuric acid group, or a salt biologically exchangeable with the foregoing groups; a monovalent blocking group derivable by removal of a hydroxyl from an aliphatic carboxyl, an aromatic carboxyl, an amino acid carboxyl, or a peptide carboxyl; and a monovalent blocking group derivable by removal of any one hydroxyl from a monosaccharide or a polysaccharide, and said BLOCK is cleaved from said substrate by the action of a specified enzyme to yield a HO—X$_{cu}$ product, and further, said HO—X$_{cu}$ product intramolecularly forms a lactone ring to provide a coumarin derivative;

wherein X$_{cu}$ has a structure represented by the following formula, the C$^7$–C$^2$ bond and the C$^8$–C$^9$ bond have trans-configuration with respect to the C$^7$=C$^8$ double bond, and the X$_{cu}$ is covalently bound to oxygen O at C$^1$ carbon,

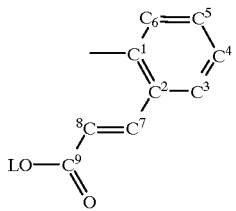

wherein L represents H, NH$_4$, alkyl having 1 to 4 carbons, tetralkylammonium having 1 to 4 carbons, or an alkaline metal or an alkaline earth metal; and further, wherein said coumarin derivative has a structure represented by the following formula:

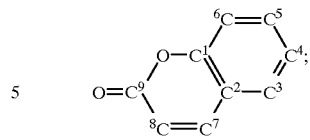

and (B) detecting said coumarin derivative.

Further, the invention provides the above-mentioned method wherein the X$_{cu}$ is a substrate in which the C$^3$–C$^4$ bond forms a 5- or 6-membered aromatic ring; H is bound to C$^5$, C$^6$, and C$^7$; and H or CH$_3$ is bound to C$^8$.

Also, the invention provides the above-mentioned method the X$_{cu}$ is a substrate having a structure represented by the following formula:

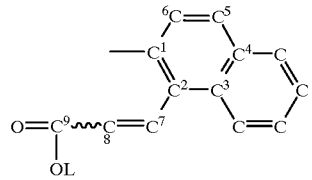

Moreover, the invention provides the above-mentioned method wherein the X$_{cu}$ is a substrate in which dialkylamino having 1 to 3 carbons is bound to C$^5$; hydrogen is bound to C$^3$, C$^4$, C$^6$, and C$^7$; and H or CH$_3$ is bound to C$^8$.

Also, the invention provides the above-mentioned method wherein the X$_{cu}$ is a substrate having a structure represented by the following formula:

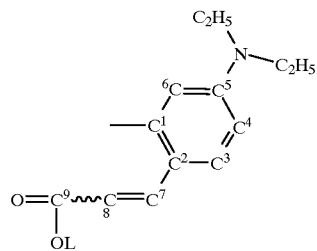

Furthermore, the invention provides the above-mentioned method wherein the X$_{cu}$ is a substrate in which alkyloxy having 1 to 3 carbons is bound to C$^3$ and C$^5$; H is bound to C$^4$, C$^6$, and C$^7$; and H or CH$_3$ is bound to C$^8$.

Also, the invention provides the above-mentioned method wherein the X$_{cu}$ is a substrate having a structure represented by the following formula:

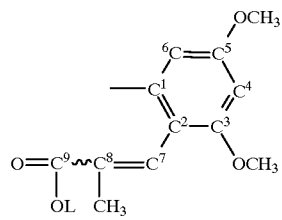

In addition, the invention provides the above-mentioned method wherein the step of detecting the coumarin derivative is to detect the fluorescence of the coumarin derivative.

Also, the invention provides the above-mentioned method that is any one of the following methods: a method for determining the activity of alkaline phosphatase wherein the BLOCK is a phosphoric acid group ($PO_3^{2-}$); a method for determining the activity of acidic phosphatase wherein the BLOCK is a phosphoric acid ($PO_3^-$); a method for determining the activity of β-galactosidase wherein the BLOCK is D-galactopyranoside; and a method for determining the activity of esterase wherein the BLOCK is acetyl ($CH_3CO$).

BEST MODE FOR CARRYING OUT THE INVENTION

Fluorescent Enzyme Substrates

Figure 1:
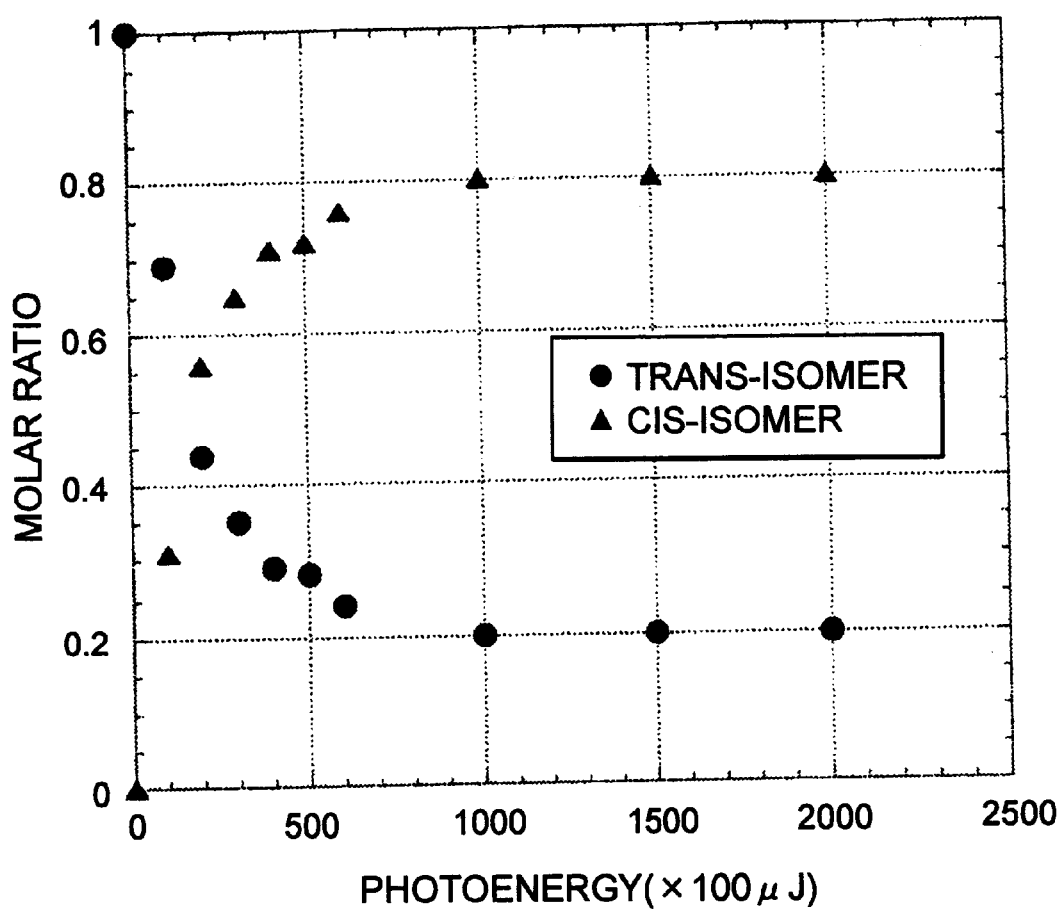
FIG. 1 is a graph showing the photoequilibrium between cis- and trans-isomers of trisodium=2-[1-(2-carboxylatoethenyl)]naphtylphosphite that is a substrate according to this invention.

The fluorescent enzyme substrate (or simply referred to as "enzyme substrate") according to this invention has a structure wherein one group (represented by "BLOCK") that dissociates as a result of a specific enzyme reaction for which the activity is to be determined and the other ($X_{cu}$) group that dissociates as the result of said enzyme reaction are covalently bonded through oxygen. Namely, the enzyme substrate is represented by the following formula:

(BLOCK-O-)-$X_{cu}$

Such enzyme substrate yields BLOCK-OH and OH—$X_{cu}$ as products when the BLOCK group is cleaved by the specific enzyme reaction.

Moreover, in the enzyme substrate according to this invention, the HO—$X_{cu}$ product from the aforementioned enzyme reaction further has a structure that intramolecularly forms a lactone ring to give a coumarin derivative. Then, the hydroxyl (OH) formed as a result of the enzyme reaction disappears by being involved in the lactone ring formation.

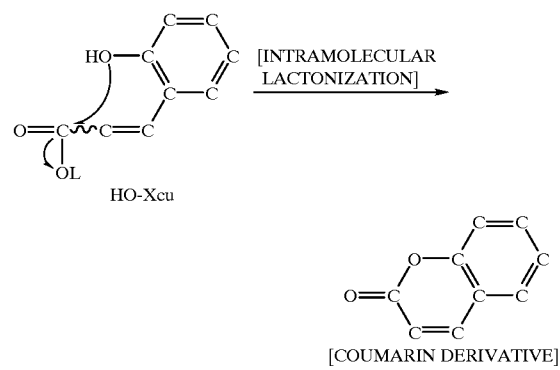

Also, the HO—$X_{cu}$ product has a structure that forms a derivative (coumarin derivative) having a coumarin skeleton through such lactone ring formation. The coumarin derivative thus obtained displays strong fluorescence in solution.

Therefore, as the specific enzyme reaction proceeds through the use of the enzyme substrate according to this invention, it becomes possible to observe the fluorescence arising from the above-mentioned coumarin derivative accordingly.

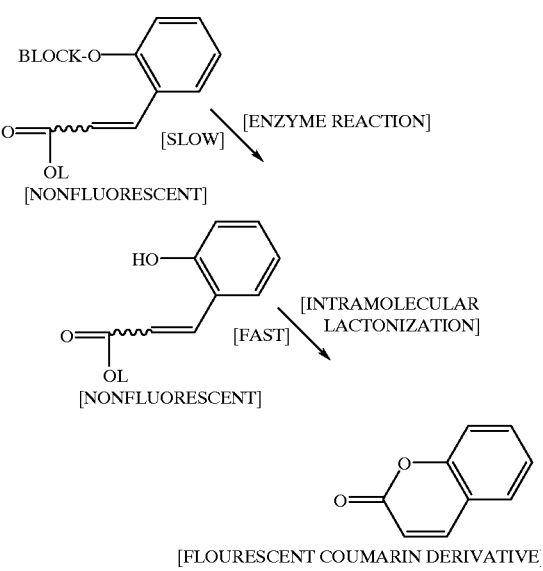

Thus, the types of "BLOCK" groups which are usable in this invention are not particularly limited insofar as they are substrates specific to the enzyme the activity of which is to be determined, and in addition, they are cleaved to BLOCK-OH and OH—$X_{cu}$ by the enzyme reaction. Concretely, named for the BLOCK is any one blocking group selected from the following, as will be shown by the formulae below: a monovalent blocking group derivable by removal of one hydroxyl from a phosphoric acid group, a sulfuric acid group, or a salt biologically exchangeable with the foregoing groups; also, a monovalent blocking group derivable by removal of a hydroxyl from an aliphatic carboxyl, an aromatic carboxyl, an amino acid carboxyl, or a peptide carboxyl; and further, a monovalent blocking group derivable by removal of any one hydroxyl from a monosaccharide or a polysaccharide. Such blocking groups (or "BLOCK") can preferably be used to determine the enzyme activity in the enzyme reaction involving each of phosphatase, esterase, galactosidase, and the like.

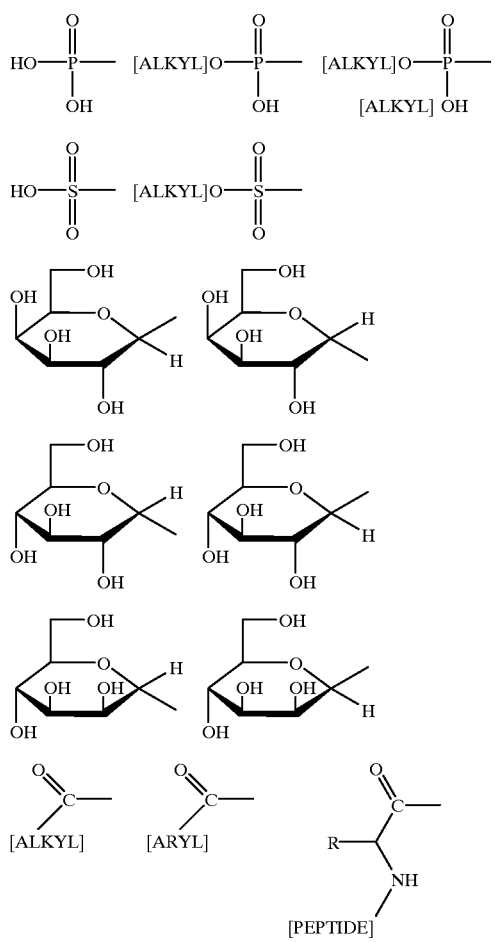

As explained above, "$X_{cu}$" groups which are usable in this invention are not also particularly limited insofar as they generate HO—$X_{cu}$ through enzyme reactions that forms a lactone ring intramolecularly to give a coumarin derivative; however, they preferably have the partial structures as described below within their chemical structures. Here, $X_{cu}$ is covalently bound to oxygen "O" at $C_1$ carbon and said oxygen is further covalently bound to the BLOCK.

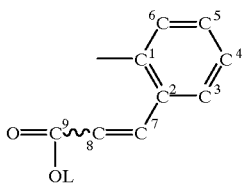

The intramolecular lactonization proceeds through the release of HOL (leaving group) into solution by the reaction between the oxygen bound to the $C^1$ carbon and the carbonyl carbon $C^9$.

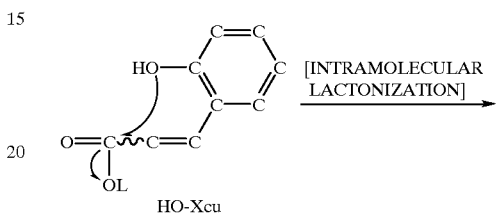

Accordingly, it is necessary that $C^2$ carbon, which is an ortho position with respect to the $C^1$ carbon of the benzene ring as described above, be substituted by a group having the structure of $C^7=C^8-C^9=O$. Here, both cis- and trans-geometrical isomers are possible, where the $C^9$ carbonyl and the benzene ring are cis or trans with respect to the double bond between the $C^7$ carbon and the $C^8$ carbon, but the cis-isomer is the one that is capable of forming a coumarin derivative through the intramolecular lactonization. Thus, the intramolecular lactonization does not proceed in the trans-isomer as such, and as a result, since the coumarin derivative can not be formed, its fluorescence can not be detected. In such case, it is possible to photoisomerize the trans-isomer to the cis-isomer by appropriate irradiation. Through irradiation during or upon completion of the enzyme reaction, the intramolecular formation of a lactone ring proceeds efficiently, thus generating the coumarin derivative.

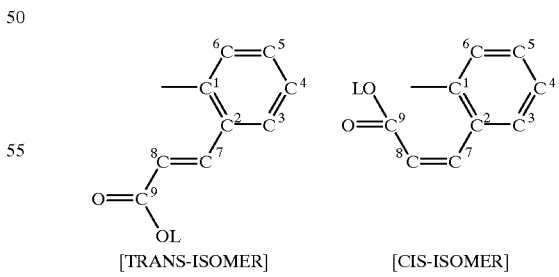

Furthermore, in the cases where there is a substituent other than H at the $C^6$ carbon, which is the other ortho position with respect to the $C^1$ carbon, the enzyme reaction often does not proceed due to its steric hindrance, and in such cases, $C^6$ may preferably be unsubstituted. Substituents other than H at the $C^3$, $C^4$, and $C^5$ carbons are not also particularly limited, and they may be the ones that allow the formation of the coumarin derivatives efficiently through the enzyme reactions. In this invention, preferred are the structures in which H is bound to $C^6$ and $C^7$, and H or $CH_3$ is bound to $C^8$.

Although there are no particular limitations to the chemical structure of L in this invention, preferably usable are H, $NH_4$, alkyl having 1 to 4 carbons (most preferably, methyl), tetralkylammonium having 1 to 4 carbons (most preferably, tetramethylammonium), an alkaline metal (most preferably, Na or K), and an alkaline earth metal (most preferably Ca).

In this invention, the $X_{cu}$ group further embraces those which have the chemical structures as described above and, in addition, the $C^3$–$C^4$ carbon bonds of which form 5- or 6-membered aromatic rings.

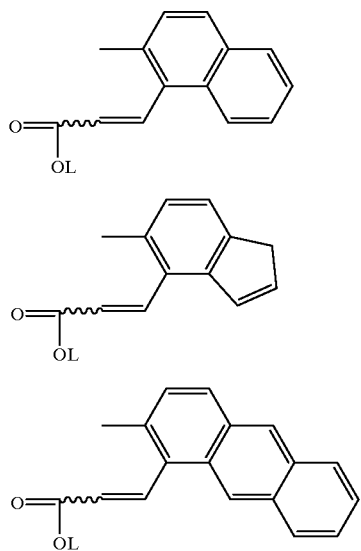

In these cases, it is possible to choose optimal structures for the resulting coumarin derivatives with respect to their excitation wavelengths, fluorescence wavelengths, fluorescence intensities, and so on. On the other hand, where too many aromatic rings are substituted, there is the possibility that the solubility of the enzyme substrate and the coumarin derivative obtained therefrom is insufficient and precipitates are formed, thus making them unsuitable for monitoring of the enzyme activity in reaction quantitatively or in real-time. The particularly preferred $X_{cu}$ group has a naphthalene skeleton, which adds one aromatic ring.

In this invention, the $X_{cu}$ group further embraces those which have the chemical structures as described above and, in addition, the $C^5$ carbons of which are substituted by alkylamino groups.

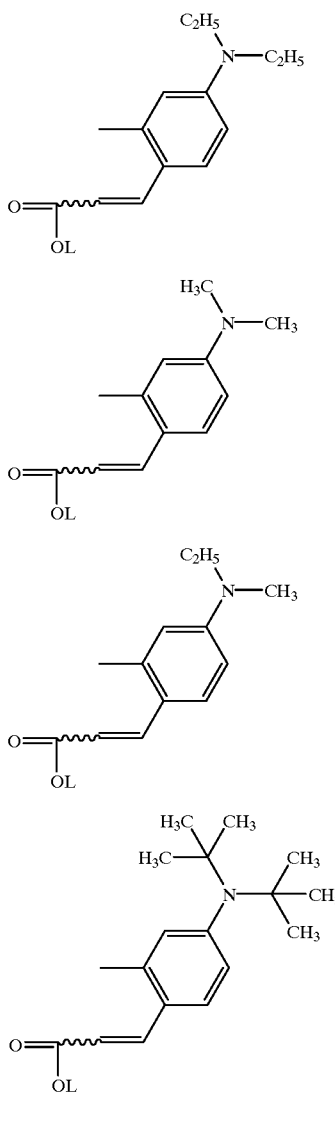

Here, R' and R" for the alkylamino group (NR'R") are preferably alkyls having 1 to 3 carbons; especially, it is preferred that R' and R' are both ethyl. As regards the introduction of such substituents of alkylamino, the choice can be possible with a view to optimizing the excitation wavelength, fluorescence wavelength, fluorescence intensity and so on for the detection of fluorescence of the resulting coumarin derivative.

In this invention, the $X_{cu}$ group further embraces those which have the chemical structures as described above and, in addition, the $C^3$ and $C^5$ carbons of which are substituted by alkyloxy having 1 to 3 carbons. As regards the introduction of such substituents of alkyloxy, the choice can be possible with a view to optimizing the excitation wavelength, fluorescence wavelength, fluorescence intensity and so on for the detection of fluorescence of the resulting coumarin derivative. Especially, methoxy can preferably be used in this invention.

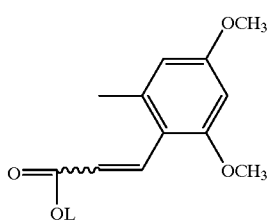

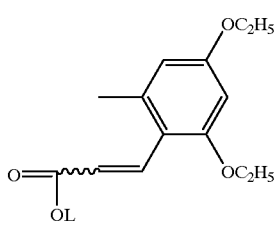

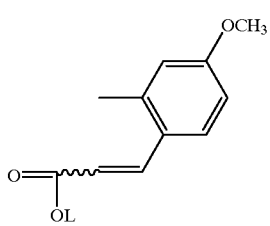

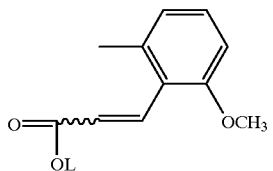

Synthetic Methods

There are no particular limitations to the synthetic methods for the fluorescent enzyme substrates according to this invention. Ordinary methods in organic synthesis known in the art can be used. As will be illustrated as an example in the scheme below, the route relying on Wittig reaction is preferable: It involves a method to introduce a double bond to the formyl group at the 1-position of a salicylaldehyde derivative (I) through a Wittig reaction. The conditions for the Wittig reaction are not particularly limited, and ordinarily known conditions can preferably be used. (G. Wittig, U. Schoellkopt, Org. Synth., Coll. Vol., V, 751 (1973).)

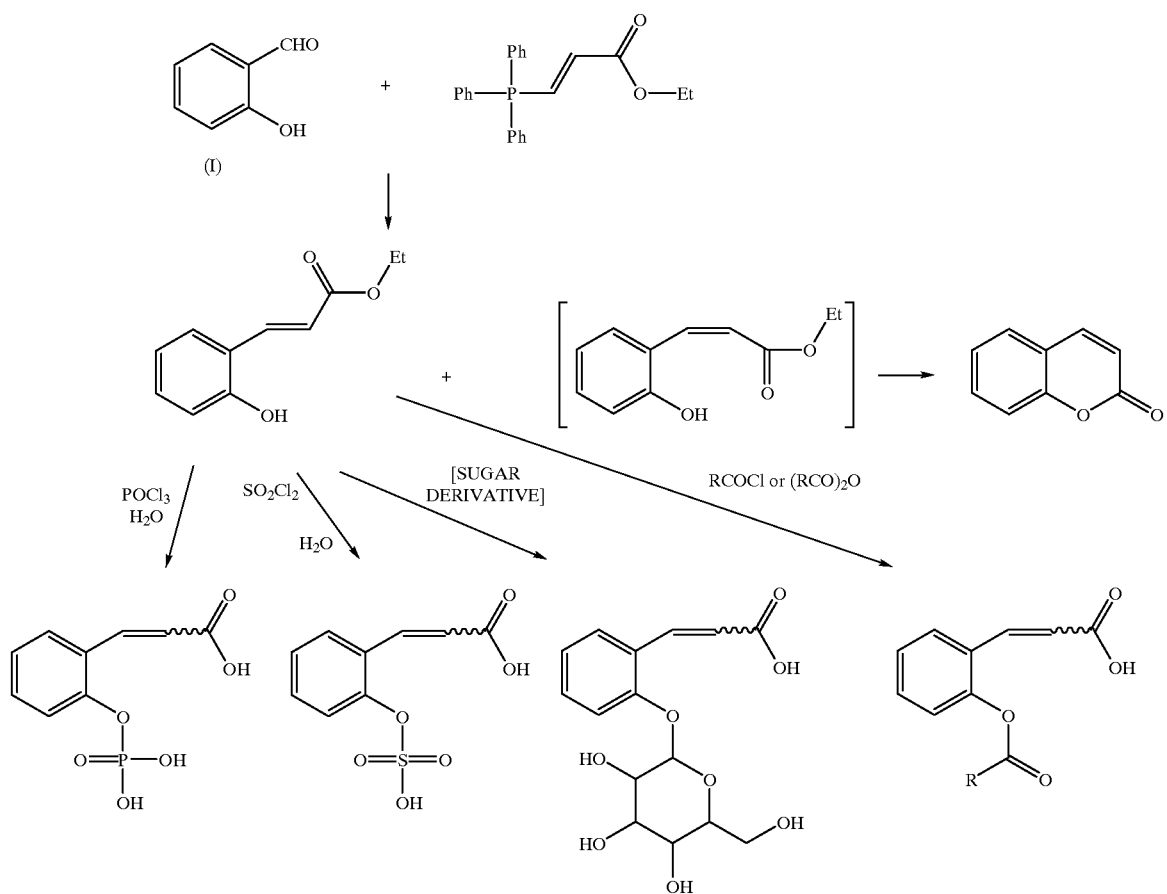

Although the reaction product is a mixture of cis- and trans-isomers with respect to the double bond, the cis-isomer instantly undergoes intramolecular cyclization to give a coumarin derivative. Thus, known separation methods can be used to isolate only the trans-isomer, and it is possible to isolate the trans-isomer in purity more than 95% by column chromatography (e.g., with aminopropyl silica gel as a column support and a hexane/ethyl acetate or chloroform/methanol system as solvent) or the like. If necessary, methods such as recrystallization may further enable purification in more than 99.5%. Structural identification of the trans-isomer is feasible according to a combination of standard techniques such as absorption spectroscopy, infrared spectroscopy (IR), nuclear magnetic resonance spectroscopy (NMR), and mass spectroscopy (MS). Specifically, the presence of a naphthalene skeleton can be confirmed by the presence or absence of a characteristic absorption spectral band. (See, Handbook of Fluorescence Spectra of Aromatic Molecules, 2nd Ed. p330, Academic Press (1971).) The formation of a double bond can be confirmed by IR spectrum characteristic of a cinnamate group (e.g., in the vicinity of 1610 and 1680 cm$^{-1}$) and NMR spectrum (e.g., double bond carbons and carbonyl carbons). Moreover, it can also be done by MS which confirms the presence of a parent peak or characteristic fragment peaks.

Although the general structural identification techniques as described above are also usable for the structural identification of the coumarin derivatives, the presence of strong fluorescence characteristic of a coumarin skeleton can be an identification tool as well. After separation on a column chromatograph, the coumarin derivative can be further made into a purified product in purity of more than 99.5% by recrystallization from ethanol (or hexane/ethyl acetate). The coumarin derivative can be used in the calibration of fluorescence intensities as a reference material during the determination of enzyme activities employing the substrates according to this invention.

It is easy to introduce a required substituent at the phenolic OH group of the resulting trans-isomer. For a phosphoric acid group, the method as described in W. Morozowich, et al., Journal of Pharmaceutical Sciences, 58, 1485–1489 (1969) can preferably be used, for example. For a D-galactopyranosyloxy group, the method as described in Manabu Nakazono, Hitoshi Nohta, Kazumi Sasamoto and Yosuke Ohkura, Analytical Sciences, 8, 779–783 (1992) can preferably be used, for example. Also, for an acetyl group, the method as described in Organic Synthesis, Coll. Vol., III, 452 (1955) can preferably be used, for example. Further, for a sulfuric acid group, the method as described in J. Freigenbaum, C. A. Neuberg, J. Am. Chem. Soc., 63, 3529 (1941) can preferably be used, for example.

One concrete example of the introduction of a phosphoric acid group preferably involves reaction with phosphorous oxychloride and further hydrolysis under standard conditions. Structural identification of the reaction product is possible by confirming the disappearance of absorption characteristic of OH and the appearance of absorption characteristic of a phosphoric acid group in IR. At this juncture, the carboxylic acid ester group is simultaneously hydrolyzed.

Structural identification of the resulting acid derivative is also possible by confirming the disappearance of absorption characteristic of an ester group and the appearance of absorption characteristic of a phosphoric acid group in IR. In addition, isolation in a salt form is also possible by neutralization with an appropriate alkaline solution. Considering the ease in the preparation of substrate solutions and their stability in storage, trisodium salts are preferable.

For one concrete example of the introduction of a D-galactopyranosyloxy group, a usable method is as follows: after the proton of a phenolic hydroxyl has been treated with a strong base such as sodium hydride, it is allowed to react with tetracetyl-α-D-galactopyranosyl bromide, and the acetyl groups, which are protecting groups for sugar hydroxyl groups, are removed for deprotection with a weak base such as sodium methoxide.

For one concrete example of the introduction of an acetyl, a usable method involves reaction, in the presence of a base such as pyridine, with an anhydride of a carboxylic acid that corresponds to an acyl to be introduced.

Methods for Determining Enzyme Activities

The methods for determining enzyme activities according to this invention are those which use enzyme substrates according to the invention as explained above that specifically react in certain enzyme reactions. Namely, the method comprises the step of treating a sample containing an enzyme to be detected, with an enzyme substrate represented by the formula below and the step of detecting the aforementioned coumarin derivative.

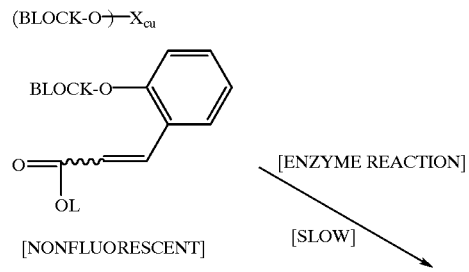

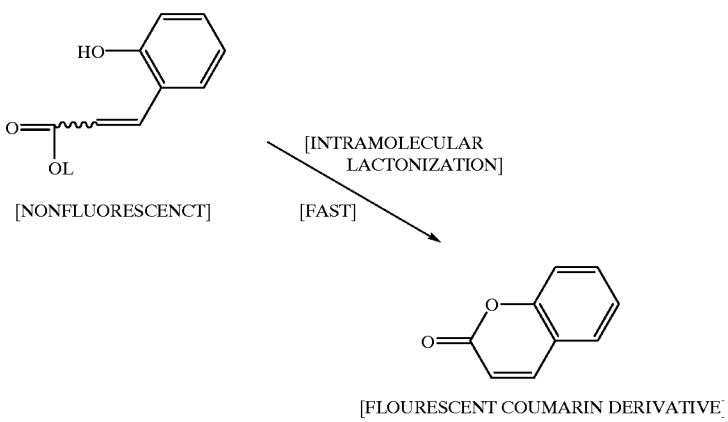

Through the treatment of the enzyme with the enzyme substrate, the substrate is subjected to enzymatic hydrolysis, yielding BLOCK-OH and OH—$X_{cu}$. Further, the OH—$X_{cu}$ thus generated forms a coumarin derivative by way of intramolecular lactonization, and because the coumarin derivative is strongly fluorescent, it becomes possible to determine the enzyme activity in reaction by detecting such fluorescence.

Namely, the rate of the enzyme reaction according to this invention is sufficiently slow as compared to the reaction rate of the intramolecular lactonization, and it becomes possible to determine the reaction rate of the enzyme reaction, that is, the enzyme activity by measuring the fluorescence intensity arising from the coumarin derivative generated in the reaction solution.

Also, the types of enzymes which can be measured in this invention are not particularly limited and it may suffice that they cleave the enzyme substrates according to this invention into BLOCK-OH and OH—$X_{cu}$ through the enzyme reactions. The enzymes accompanying such enzyme reactions contain, for example, a large number of hydrolases. Concretely, the enzyme activities for the enzyme reactions involving alkaline or acid phosphatase, sulfatase, galactosidase, esterase and the like can be determined by employing the enzyme substrates according to this invention that specifically react with the respective enzymes.

Namely, the enzyme substrates the BLOCK groups of which are defined in the following can be used: for alkaline or acid phosphatase, the BLOCK group is a phosphoric acid or an ester thereof; for sulfatase, the BLOCK group is a sulfuric acid or an ester thereof; for galactosidase, the BLOCK group is a monosaccharide or polysaccharide; and for esterase, the BLOCK group is an aliphatic carboxyl, an aromatic carboxyl, an amino acid carboxyl or a peptide carboxyl.

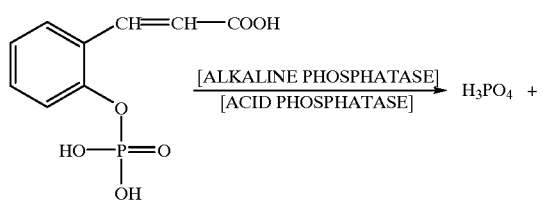

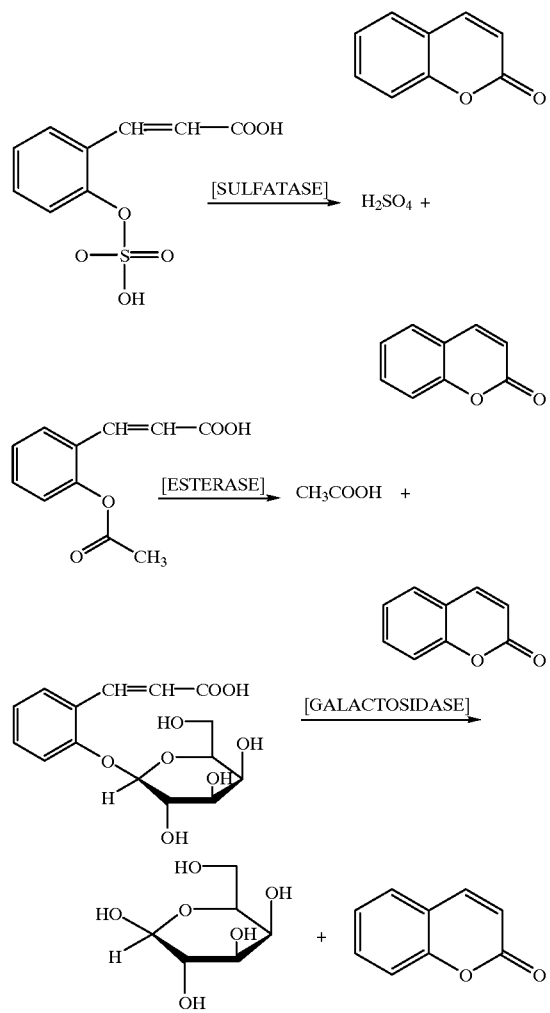

Moreover, when the enzyme activities in reaction are to be determined with respect to specified enzymes in this invention, it becomes possible to measure the enzymes having a variety of different enzyme reaction rates by selecting enzyme substrates having a variety of different substituents for use among those explained above according to this invention. In this connection, the selection can be made based on differences between Km values for the enzyme substrates having the respective substituents and Km values for cis- and trans-isomers of the enzyme substrates according to this invention as will be illustrated below: generally, a trans-isomer has a smaller Km value than a cis-isomer.

[SUBSTRATE FOR β-D-GALACTOSIDASE]

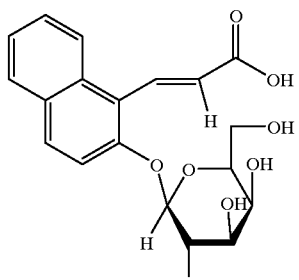

[TRANS-ISOMER]
Km = 0.07mM

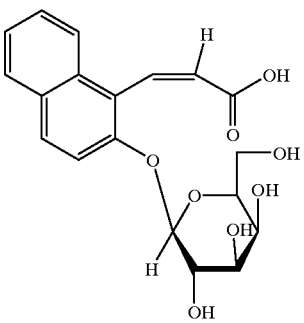

[CIS-ISOMER]
Km = 0.53mM

[SUBSTRATE FOR PHOSPHATASE]

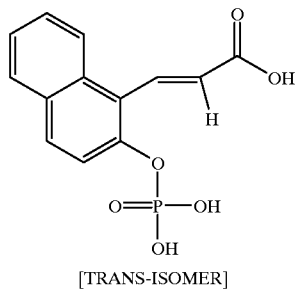

[TRANS-ISOMER]

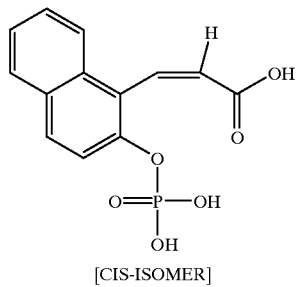

[CIS-ISOMER]

-continued

| target enzyme | trans-isomer | trans- and cis-isomers mixture |
|---|---|---|
| alkaline phosphatase | Km = 0.14 mM | Km = 0.50 mM |
| acidic phosphatase | Km = 0.23 mM | KM = 1.51 mM |

Where an enzyme substrate having a small Km value is selected, it normally becomes possible to decrease the amount of the substrate in the determination of the activity of the desired enzyme because of the property of Km values. The reactivity for an enzyme substrate can be determined by measuring its Km value in accordance with standard conditions.

In the method for determining the enzyme activity in reaction by means of the enzyme substrate that is a cis-isomer, the irradiation conditions as described above will not be required because after the enzyme substrate is cleaved by the enzyme reaction, it forms a coumarin derivative by way of intramolecular lactonization. On the other hand, with the enzyme substrate that is a trans-isomer, OH-$X_{cu}$ generated by the enzyme reaction does not by itself undergo the intramolecular lactonization; therefore, it does not enable the measurement of the fluorescence that will arise from the coumarin derivative. In this case, the conditions that will allow irradiation of the enzyme reaction system are required. In this invention, the term, "treating under irradiation" means such irradiation conditions. In other words, the trans-isomer changes into the cis-isomer because the photoequilibrium between the trans-isomer and the cis-isomer is established under the irradiation conditions. Since the cis-isomer undergoes the intramolecular lactonization, the photoequilibrium shifts from the trans-isomer to the cis-isomer, and as a result, all the trans-isomer turns the cis-isomer which undergoes the lactonization.

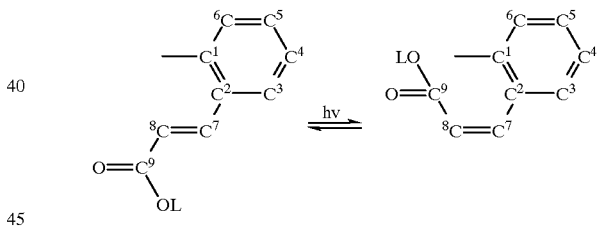

Namely, in an embodiment where the substrate that is a trans-isomer is used, the enzyme reaction is first carried out under the conditions without irradiation, and the enzyme reaction is terminated after a period of appropriate time. Irradiation of the resulting reaction solution isomerizes OH—$X_{cu}$ that is a trans-isomer existing in the solution to its cis-isomer, which generates a coumarin derivative by way of intarmolecular lactonization; the measurement of its fluorescence is thus possible. In this case, OH—$X_{cu}$ is present in the enzyme solution prior to the irradiation, which implies that the enzyme reaction product having a phenolic OH is present. In another embodiment where the substrate that is a trans-isomer is used, the method involves carrying out the enzyme reaction under the irradiation conditions and measuring the fluorescence of the coumarin derivative in the resulting reaction solution. Such irradiation conditions may be made possible by the use of an ordinary irradiation device. However, no particular irradiation device for the irradiation is needed under the standard enzyme reaction conditions, because the photoisomerization takes place easily. The irradiation conditions achieved by a room lamp (including a fluorescence lamp) are even sufficient. The particular irradiation device may concretely employ a 15 W mercury discharge tube (365 nm) and irradiation with it for about one minute enables the quantitative isomerization to cis-isomers.

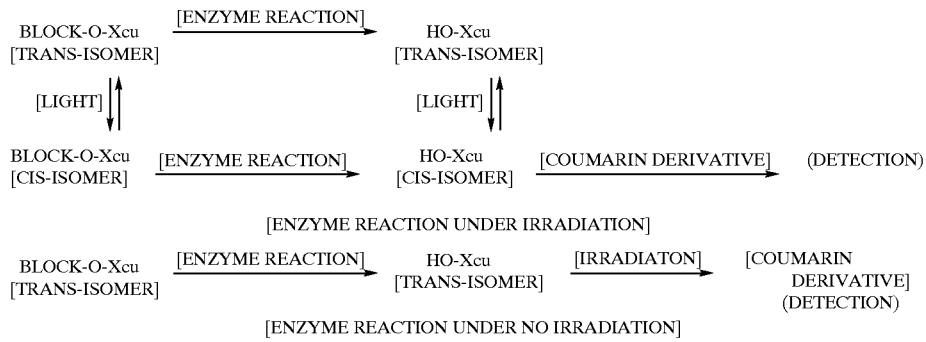

As explained above, the method according to this invention makes it possible to measure a comparatively slow enzyme reaction based on the measurement of fluorescence resulting from formation of the coumarin derivative and to measure the initial velocity of the enzyme reaction. By employing the above-mentioned enzyme substrate that is a cis-isomer or the substrate that is a trans-isomer under the irradiation conditions, it becomes possible to monitor the enzyme reaction in real-time without stopping said enzyme reaction. Furthermore, because in this case no phenolic products are present in the reaction solution, the inhibitory action on the enzyme reaction due to the accumulation of phenolic products, which is common, can then be suppressed. This effect will allow the enzyme reaction to be monitored from its initial stage over a sufficiently long time.

Further, the method may preferably be used in the case employing the initial velocity method for enzyme activities, which is ordinarily known.

According to the method of this invention, it becomes possible to determine the activity of alkaline phosphatase or of acidic phosphatase by using the enzyme substrate of this invention the BLOCK of which is a phosphoric acid group ($PO_3^{-2}$) or a phosphoric acid ester. In this case, because the method according to this invention determines the enzyme activity through the detection of fluorescence of the coumarin derivative, effects of pH of the enzyme reaction solution are extremely small; therefore, the method has proved to be highly reproducible and also highly sensitive. Moreover, because the method relies on fluorescence measurement, the requisite concentration of the coumarin derivative which is the product of the enzyme reaction and the subject of measurement is extremely small. The coumarin derivative formed is sufficiently dissolved in solution without causing precipitation. This also allows the method according to this invention to be highly reproducible and also highly sensitive.

According to the method of this invention, it becomes possible to determine the activity of β-galactosidase by using the enzyme substrate of this invention the BLOCK of which is D-galactosidase. In this case, because the method according to this invention determines the enzyme activity through the detection of fluorescence of the coumarin derivative, effects of pH of the enzyme reaction solution are extremely small; therefore, the method has proved to be highly reproducible and also highly sensitive. Moreover, because the method relies on fluorescence measurement, the requisite concentration of the coumarin derivative which is the product of the enzyme reaction and the subject of measurement is extremely small. The coumarin derivative formed is sufficiently dissolved in solution without causing precipitation. This also allows the method according to this invention to be highly reproducible and also highly sensitive.

According to the method of this invention, it becomes possible to determine the activity of esterase by using the enzyme substrate of this invention the BLOCK of which is acetyl ($CH_3CO$). In this case, because the method according to this invention determines the enzyme activity through the detection of fluorescence of the coumarin derivative, effects of pH of the enzyme reaction solution are extremely small; therefore, the method has proved to be highly reproducible and also highly sensitive. Moreover, because the method relies on fluorescence measurement, the requisite concentration of the coumarin derivative which is the product of the enzyme reaction and the subject of measurement is extremely small. The coumarin derivative formed is sufficiently dissolved in solution without causing precipitation. This also allows the method according to this invention to be highly reproducible and also highly sensitive.

According to the method of this invention, it becomes possible to determine the activity of sulfatase by using the enzyme substrate of this invention the BLOCK of which is a sulfuric acid group or a sulfuric acid ester group. In this case, because the method according to this invention determines the enzyme activity through the detection of fluorescence of the coumarin derivative, effects of pH of the enzyme reaction solution are extremely small; therefore, the method has proved to be highly reproducible and also highly sensitive. Moreover, because the method relies on fluorescence measurement, the requisite concentration of the coumarin derivative which is the product of the enzyme reaction and the subject of measurement is extremely small. The coumarin derivative formed is sufficiently dissolved in solution without causing precipitation. This also allows the method according to this invention to be highly reproducible and also highly sensitive.

EXAMPLES

This invention will be hereinbelow concretely illustrated by way of examples; however, it is not to be limited to the following examples insofar as it does not depart from its essence.

Synthesis of (E)3-(2-hydroxy-1-naphtyl)-2-pronenoic acid ethyl ester

2-Hydroxy-1-naphtylaldehyde (29.27 g, 0.17 mol; Tokyo Kasei Ind. Co. Ltd.) and carboxymethylidene-triphenylphosphorane (60 g, 0.17 mol; Aldrich Inc.) were stirred in 360 ml of benzene at 0° C. for 18 h under a nitrogen atmosphere and the reaction was allowed to be complete, during which period the reaction was conducted in a dark room. Then, the solvent was removed in vacuo, and the resulting crude product was chromatographed on a silica gel column (hexane/ethyl acetate 2:1 as a developing solvent) to remove triphenylphosphine oxide therein, affording 40.7 g of product. To further purify the product, benzocoumarin derivatives and others were removed using an aminopropionate silica gel column (hexane/ethyl acetate 2:1 as a developing solvent) and 3-(2-hydroxy-1-naphtyl)-2-propenic acid ethyl ester remaining on the column was eluted with the developing solvent (chloroform/methanol 10:1) to give 33.8 g of the desired product in 82% yield.

Structural identification of the obtained 3-(2-hydroxy-1-naphtyl)-2-propenic acid ethyl ester was conducted by $^1$H-NMR and IR spectra, and its molecular weight was confirmed by TOF-MS (MALDI-IV, 256.1 (M/C); Shimadzu Mfg. Co. Ltd).

$^1$H-NMR Data (deuteriochloroform, δ(ppm); 8.35 (d, 1H, 3-proton of the propenic acid), 8.04 (d, 1H, 5-, or 8-proton of the naphthalene ring), 7.77 (d, 1H, 5-, 8- or 4-proton of the naphthalene ring), 7.75 (d, 1H, 5-, 8- or 4-proton of the naphthalene ring), 7.52 (dd, 1H, 6- or 7-proton of the naphthalene ring), 7.37 (d, 1H, 6- or 7-proton of the naphthalene ring), 7.16 (d, 1H, 3-proton of the naphthalene ring), 6.81 (d, 1H, 2-proton of the propenic acid), 4.35 (q, 2H, methylene protons of the ethyl), 1.40 (t, 3H, methyl protons of the ethyl). IR Data; 1670 cm$^{-1}$ (ethyl ester).

Synthesis of 2-[1-(2-carboxyethenyl)]naphtylphosphate 3-(2-Hydroxy-1-naphtyl)2-propenic acid ethyl ester(10.0 g) was dissolved in 100 ml of benzene. After ice-cooling, 4.0 g of pyridine was added and 7.7 g of phosphorus oxychloride was further added dropwise over 30 min at about 5° C. under a nitrogen atmosphere, and then, it was allowed to react for about 18 h. The pyridine salt precipitated afterward was filtered off, and the solvent was removed in vacuo to give the crude product as a brown tar substance. Further, 50 ml of water was added to decompose the excess phosphorus oxycloride. Subsequently, 100 ml of 2N aqueous sodium hydroxide solution was added and allowed to react at 40° C. for 1 h. After hydrolysis, 6N hydrochloric acid was further added to adjust the pH to 1 and ice-cooled. Crystals thus precipitated were collected with a glass filter. The resulting crystals were washed with cooled water several times. The obtained crystals were hygroscopic and thus, were converted to the sodium salt as described below.

Synthesis of trisodium 2-[1-(2-carboxylatoethenyl)] naphtylphosphite

After 2-[1-(2-carboxyethenyl)]naphtylphosphate as obtained above was dissolved in water in turbidity, one equivalent of 1N sodium hydroxide was added, the resulting aqueous solution was lyophilized to remove water, and 9.2 g of the desired product was obtained as a trisodium salt in 76% yield.

The structural identification was conducted by $^1$H-NMR and IR spectra, and the molecular weight was confirmed by TOF-MS (MALDI-IV, 256.1 (M/C); Shimadzu Mfg. Co. Ltd). $^1$H-NMR Data (deuteriosulfoxide, δppm); 8.21 (d, 1H, 1-proton of the ethenyl ), 8.04 (d, 1H, 3-, 4-, 5-, or 8-proton of the naphthalene ring), 7.83 (d, 2H, 3-, 4-, 5- or 8-proton of the naphthalene ring), 7.54 (dd, 1H, 6- or 7-proton of the naphthalene ring), 7.37 (dd, 1H, 6- or 7-proton of the naphthalene ring), 7.26 (d, 1H, 3-, 4-, 5-, or 8-proton of the naphthalene ring), 6.79 (d, 1H, 2-proton of the ethenyl). IR Data; 1115, 980 cm$^{-1}$ (—OPO$_3^{2-}$ group), 1639, 1562, 1369 cm$^{-1}$ (carboxylate).

Synthesis of (E)-3-(2-tetracetyl-β-D-galactopyranosyloxy-1-naphtyl)-2-propenic acid ethyl ester (E)-3-(2-Hydroxy-1-naphtyl)-propenic acid ethyl ester was dissolved in 20.0 ml of dimethylformamide under a nitrogen atmosphere. To this was added 840 mg of sodium hydride (about 60% dispersion in paraffin) and it was stirred at room temperature for 2 h. After cooling to 0° C., 5.0 g of tetracetyl-α-D-galactopyranosyl bromide (Sigma Inc.) dissolved in dimethylformamide (10.0 mg) was added, and it was allowed to react under stirring for 1 h. Then, dimethylformamide was removed and ethyl acetate (200 ml) was added to the residue. The ethyl acetate layer was washed with water, and saturated brine, successively. To this was added anhydrous sodium sulfate and allowed to stand overnight to effect drying. Subsequently, the solvent was removed in vacuo to give a brown oily substance which was purified by silica gel chromatography (ethyl acetate/hexane 2:1 to 1:1 as a developing solvent) to give 5.75 g of the desired product.

$^1$H-NMR (deuteriochloroform, δppm); 8.12 (d, 1H, 3-proton of the propenic acid), 8.12 (d, 1H, 5-, or 8-proton of the naphthalene ring), 7.83 (d, 2H, 4-proton of the naphthalene ring and 5-or 8-proton of the naphthalene ring), 7.54 (dd, 1H, 6- or 7-proton of the naphthalene ring), 7.39 (d, 1H, 4-proton of the naphthalene ring), 6.52 (d, 1H, 2-proton of the propenic acid), 5.62 (dd, 1H, 2-proton of the galactopyranoside), 5.49 (d, 1H, 4-proton of the galactopyranoside), 5.13–5.09 (dd, 2H, 1- and 3-protons of the galactopyranoside), 4.36 (q, 2H, methylene protons of the ethyl), 4.31–4.09 (m, 3H, 5- and 6-protons of the galactopyranoside), 2.22 (s, 3H, methyl protons of an acetyl), 2.09 (s, 3H, methyl protons of an acetyl), 2.04 (s, 3H, methyl protons of an acetyl), 2.02 (s, 3H, methyl protons of an acetyl), 1.40 (t, 3H, methyl protons of the ethyl).

Synthesis of (E)-3-(2-β-D-galactopyranosyloxy-1-naphtyl)-2-propenic acid ester (E)-3-(2-Tetracetyl-β-D-galactopyranosyloxy-1-naphtyl)-2-propenic acid ethyl ester was dissolved in 100 ml of methanol. To this was added 10 ml of 28% sodium methoxide-methanol solution (Wako Chemicals Co. Ltd.) and it was stirred at room temperature for 4 h. Further, 2N sodium hydroxide aqueous solution (50 ml) was added and it was allowed to react at 60° C. for 2 h. The white crystals precipitated were filtered off and washed with water to give 3.6 g of the desired product in about 80% yield.

$^1$H-NMR (deuteriosulfoxide, δ(ppm); 8.18 (d, 1H, 3-proton of the propenic acid), 8.12 (d, 1H, 5-, or 8-proton of the naphthalene ring), 7.96 (d, 1H, 4-, 5-, or 8-proton of the naphthalene ring), 7.91 (d, 1H, 4-, 5-, or 8-proton of the naphthalene ring), 7.58 (dd, 1H, 6- or 7-proton of the naphthalene ring), 7.54 (d, 1H, 3-proton of the naphthalene ring), 7.44 (d, 1H, 6- or 7-proton of the naphthalene ring), 6.75 (d, 1H, 2-proton of the propenic acid), 5.13 (d, 1H, 1-proton of the galactopyranoside), 3.76–3.59 (m, 5H, 2-, 4-, 5-, and 6-protons of the galactopyranoside), 3.49(dd, 1H, 3-proton of the galactopyranoside).

Synthesis of (E)-3-(2-β-D-galactopyranosyloxy-1-naphtyl)-2-propenic acid ethyl ester (E) -3- (2-β-D-Galactopyranosyloxy-1-naphtyl)-2-propenic acid ethyl ester was dissolved in 100 ml of ethanol. To this was added 16.35 g of 20% sodium ethoxide-ethanol solution at room temperature and it was allowed to react under stirring overnight. The completion of reaction was confirmed by thin layer silica gel chromatography. Acidic ion exchange resin (Amberlist 15E) was slowly added to the reaction solution which was made neutral. After the ion exchange resin was filtered off, the filtrate was concentrated to about half the volume. The crystals precipitated were filtered off to give 1.93 g of the desired product in 60% yield $^1$H-NMR (deuteriodimethylsulfoxide, δppm); 8.25 (d, 1H, 3-proton of the propenic acid), 8.12 (d, 1H, naphthalene ring proton), 7.93 (d, 1H, naphthalene ring proton), 7.60 (dd, 1H naphthalene ring proton), 7.56 (d, 1H, naphthalene ring proton), 7.45 (dd, 1H, naphthalene ring proton), 6.83 (d, 1H, 2-proton of the propenic acid), 5.19–5.15 (m, 2H, 1- and 5-protons of the galactopyranoside), 4.68–4.62 (m, 2H, galactopyranoside protons), 4.25 (q, 2H, methylene protons of the ethyl), 3.75–3.66 (m, 3H, 3-protons of the galactopyranoside), 1.31 (t, 3H, methyl protons of the ethyl).

Synthesis of (E)-2-propenic acid ethyl ester (E)-3-(2-Hydroxy-1-naphtyl)-2-propenic acid ethyl ester (1.00 g, 4.13 mmol) was dissolved in 5 ml of dry pyridine. To this was added 0.8 ml (8.26 mmol) of anhydrous acetic acid and it was allowed to react at room temperature for 24 h. After water was added to the reaction system, diethyl ether was added and the diethyl ether layer was separated, which was washed with water several times. To this was added anhydrous sodium sulfate and it was dried and allowed to stand overnight. Subsequently, the solvent was removed in vacuo to give a crude product. This was recrystallized from ethanol to give 1.15 g of the desired product in 97.8% yield.

$^1$H-NMR (deuteriochloroform, δppm); 8.10 (d, 1H, 5-, or 8-proton of the naphthalene ring), 8.09 (d, 1H, 3-proton of the propenic acid), 7.86 (d, 2H, 4-proton of the naphthalene ring and 5- or 8-proton of the naphthalene ring), 7.57 (dd, 1H, 6- or 7-proton of the naphthalene ring), 7.53 (dd, 1H, 6- or 7-proton of the naphthalene ring), 7.23 (d, 1H, 3-proton of the naphthalene ring), 6.45 (d, 1H, 2-proton of the propenic acid), 4.32 (q, 2H, methylene protons of the ethyl), 2.36 (s, 3H, methyl protons of the acetyl), 1.37 (s, 3H, methyl protons of the ethyl).

Synthesis of 3-(4-diethylamino-2-hydroxyphenyl)-2-propenic acid ethyl ester

4-Diethylaminosalicylaldehyde (25.0 g, 129 mmol; Tokyo Kasei Ind. Co. Ltd.) and carboxymethylidene-triphenylphosphorane (49.0 g, 140 mmol; Aldrich Inc.) were stirred in 300 ml of anhydrous benzene at room temperature overnight under a nitrogen atmosphere and the reaction was allowed to complete, during which period the reaction was conducted in a dark room. Then, the solvent was removed in vacuo, and the resulting crude product was crudely purified by silica gel column chromatography (hexane/ethyl acetate 1:1 as a developing solvent) to give a mixture of cis- and trans-isomers. Further, this mixture was purified by column chromatography using aminopropyl-modified silica gel (300 g of NHDM-1020 silica gel available from Fuji Silicia Chemicals Co. Ltd; n-hexane/ethyl acetate 2:1 which elutes only the cis-isomer and chloroform/methanol 4:1 which elutes only the trans-isomer) to give 23.7 g of the desired product in 70% yield.

The structure of the obtained 3-(4-diethylamino-2-hydroxyphenyl)-2-propenic acid ethyl ester was confirmed by $^1$H-NMR.

$^1$H-NMR (deuteriochloroform, δppm); 7.91 (d, 1H, 3-proton of the propenic acid), 7.31 (d, 1H, 5-, or 6-proton of the benzene ring), 6.35 (d, 1H, 2-proton of the propenic acid), 6.25 (d, 1H, 5-, or 6-proton of the benzene ring), 6.06 (s, 1H, 3-proton of the benzene ring), 4.25 (q, 2H, methylene protons of the ethyl ester group), 3.35 (q, 4H, methylene protons of the diethylamino), 4.65 (s, 1H, proton of the phenolic hydroxyl), 1.33 (t, 3H, methyl protons of the ethyl ester group), 1.17 (t, 6H, methyl protons of the diethylamino).

Synthesis of 2-[1-(2-carboxyethenyl)]5-diethylamino-phenylphosphite 3-(4-Diethylamino-2-hydroxyphenyl)-2-propenic acid ethyl (13 g, 40.9 mmol) and benzene (200 ml) were ice-cooled in a reactor, to which was dropwise added 9.0 g (59 mmol) of phosphorus oxychloride (Wako Pure Chemicals Co. Ltd.) over about 30 min. The reaction was completed by stirring overnight. The completion of reaction was confirmed by thin layer chromatography. A small amount of water was added to the reaction solution to treat the excessive phosphorus oxychloride and the majority of the benzene solvent was removed in vacuo. Then, the remaining aqueous solution was neutralized (pH 8) with methanol (50 ml) and 6N sodium hydroxide aqueous solution, and further, the aqueous solution was washed with ethyl acetate several times. Subsequently, the solvent was removed in vacuo to give a solid residue. The resulting residue was extracted with chloroform and chloroform was removed to give a residue, to which 200 ml of water was added to dissolve. Insoluble materials were removed by filtration and the resulting aqueous solution was lyophilized to give 12.9 g of the desired product in a quantitative yield.

The structure of the obtained 2-[1-(2-carboxyethenyl)]5-diethylaminophenylphosphite was confirmed by $^1$H-NMR.

$^1$H-NMR (deuteriowater, δppm); 8.00 (d, 1H, 1-proton of the ethenyl), 7.53 (d, 1H, 3-, or 4-proton of the benzene ring), 6.90 (d, 1H, 6-proton of the benzene ring), 6.56 (d, 1H, 3-, or 4-proton of the benzene ring), 6.36 (d, 1H, 2-proton of the ethenyl), 4.24 (q, 4H, methylene protons of the diethylamino), 1.31 (t, 6H, methyl protons of the diethylamino).

Synthesis of 3-(2-acetoxy-4-diethylaminophenyl)-2-propenic acid ethyl ester 3-(4-Diethylaminophenyl)-2-propenic acid ethyl ester (1 g, 3.80 mmol) was dissolved in 5 ml of pyridine. To this was added 0.8 ml of anhydrous acetic acid and it was allowed to react at room temperature for 24 h. After the solvent was removed in vacuo, purification was carried out by silica gel column chromatography (toluene/ethyl acetate 93:7 as a developing solvent) to give 1.2 g of the desired product in a quantitative yield.

The structure of the obtained 3-(2-acetoxy-4-diethylaminophenyl)-2-propenic acid ethyl ester was confirmed by $^1$H-NMR, and its molecular weight was further confirmed by TOF-MS (MALDI-IV, 305(M/C); Shimadzu Mfg. Co. Ltd).

$^1$H-NMR (deuteriochloroform, δppm); 7.63 (d, 1H, 3-proton of the propenic acid group), 7.48 (d, 1H, 5'-, or 6'-proton of the benzene ring), 6.52 (d, 1H, 5'- or 6'-proton of the benzene ring), 6.28 (s, 1H, 3'-proton of the benzene ring), 6.20 (d, 1H, 2-proton of the propenic acid group), 4.22 (q, 2H, methylene protons of the ethyl ester group), 3.36 (q, 4H, methylene protons of the diethylamino group), 2.37 (s, 3H, methyl protons of the acetoxy group), 1.31 (t, 3H, methyl protons of the ethyl ester group), 1.18 (t, 6H, methyl protons of the diethylamino).

Synthesis of 3-(4,6-dimethoxy-2-hydroxyphenyl)-2-methyl-2-propenic acid ethyl ester 4,6-Dimethoxysalicylaldehyde (30.0 g, 165 mmol; Aldrich Inc.) and carboxyethylidene-triphosphorane (60.0 g, 166 mmol; Aldrich Inc.) were stirred in 300 ml of anhydrous benzene at room temperature overnight under a nitrogen atmosphere and the reaction was allowed to complete, during which period the reaction was conducted in a dark room. Then, the benzene solvent was removed in vacuo to give a crudely purified product. The resulting crude product was crudely purified by silica gel column chromatography (hexane/ethyl acetate 1:1 as a developing solvent) to give a mixture of cis- and trans-isomers. The thus obtained mixture was purified by column chromatography using aminopropyl-modified silica gel (300 g of NHDM-1020 silica gel available from Fuji Silicia Chemicals Co. Ltd; n-hexane/ethyl acetate 2:1 which elutes only the cis-isomer and chloroform/methanol 4:1 which elutes only the trans-isomer) to give 35.4 g of the desired product in 81% yield.

The structure of the obtained 3-(4,6-dimethoxy-2-hydroxyphenyl)-2-methyl-2-propenic acid ethyl was confirmed by $^1$H-NMR.

$^1$H-NMR (deuteriochloroform, δppm); 7.54 (d, 1H, 3-proton of the propenic acid), 6.17 (s, 1H, 3'-, or 5'-proton of the benzene ring), 6.06 (s, 1H, 3- or 5'-proton of the benzene ring), 4.23 (q, 2H, methylene protons of the ethyl ester group), 3.76 (s, 3H, methyl protons of a methoxy), 3.75 (s, 3H, methyl protons of a methoxy), 1.85 (s, 3H, methyl protons at the 2-position of the propenic acid), 1.32 (t, 3H, methyl protons of the ethyl ester group).

Synthesis of 3-(2-acetoxy-4, 6-dimethoxyphenyl)-2-methyl-2-propenic acid ethyl ester 3-(4,6-Dimethoxyphenyl)-2-methyl-2-propenic acid ethyl ester (1 g, 3.76 mmol) was dissolved in 5 ml of pyridine. To this was added 0.8 ml of anhydrous acetic acid and it was allowed to react at room temperature for 24 h. After the solvent was removed in vacuo, purification was carried out by silica gel column chromatography (toluene/ethyl acetate 93:7 as a developing solvent) to give 1.2 g of the desired product in a quantitative yield.

The structure of the obtained 3-(2-acetoxy-4, 6-dimethoxyphenyl)-2-methyl-propenic acid ethyl was confirmed by $^1$H-NMR.

$^1$H-NMR (deuteriochloroform, δppm); 7.34 (s, 1H, 3-proton of the propenic acid), 6.38 (s, 1H, 3'- or 5'-proton of the benzene ring), 6.28 (s, 1H, 3'- or 5'-proton of the benzene ring), 4.24 (q, 2H, methylene protons of the ethyl ester group), 3.79 (s, 6H, methyl protons of the methoxy groups), 2.20 (s, 3H, methyl protons of the acetoxy), 1.79 (s, 3H, methyl protons at the 2-position of the propenic acid), 1.32 (t, 3H, methyl protons of the ethyl ester group).

Photoequilibrium Experiment 1

Employing trisodium=(E) 2-[1-(2-carboxyethenyl)] naphtylphosphite that is a substrate for phosphatase according to this invention, photoisomerization of the trans-isomer to the cis-isomer by irradiation in the substrate solution for alkaline phosphatase was determined under the HPLC conditions as described below.

A solution of trisodium=(E) 2-[1-(2-carboxyethenyl)] naphtylphosphite (0.3 mmol/l) in 0.1 mol/l glycine-NaOH buffer (pH 9.5) was irradiated with UV light at 365 nm in various intensities and this was separated by high performance liquid chromatography for quantitation.

Column: TSK-gel ODS-80Ts 4.6 mm×φ7.5 mm (Toso Co. Ltd.)

Mobile phase: 7.5 mmol/l acetonitrile containing tetra-n-butylammonium dihydrogenphosphate/water 5:95

Retention time (mobile phase solvent 1 ml/min): trans-isomer (7.9 min) and cis-isomer (7.3 min)

As FIG. 1 shows, the ratio of the cis-isomer increased in proportion to the intensities of the irradiated light, and the ratio of cis-isomer to trans-isomer in terms of a molar ratio reached 1:4 under the equilibrium conditions.

A similar experiment was conducted on a composition of substrate solution for the measurement of the activity of acidic phosphatase (90 mmol/l citric acid-sodium citrate buffer (pH 4.8)). In this case, the ratio of cis-isomer to trans-isomer in terms of a molar ratio reached 1:6.7 (not shown in the figure).

Photoequilibrium Experiment 2

Employing (E) 3-[2-β-D-galactopyranosyloxy-1-naphtyl)-2-propenic acid that is a substrate for galactosidase according to this invention, photoisomerization between the trans-isomer and the cis-isomer was determined under the conditions as described below.

An aqueous solution of (E) 3-[2-β-D-galactopyranosyloxy-1-naphtyl)-2-propenic acid (0.3 mmol/l) containing 2% dimethylformamide was irradiated with UV light at 365 nm in various intensities and this was separated by high performance liquid chromatography for quantitation.

Column: TSK-gel ODS-80Ts 4.6 mm×φ7.5 mm (Toso Co. Ltd.)

Mobile phase: acetonitrile containing 2% acetic acid/water 15:85

Retention time (mobile phase solvent 1 ml/min): trans-isomer (6.9 min) and cis-isomer (5.1 min)

Figure 2:
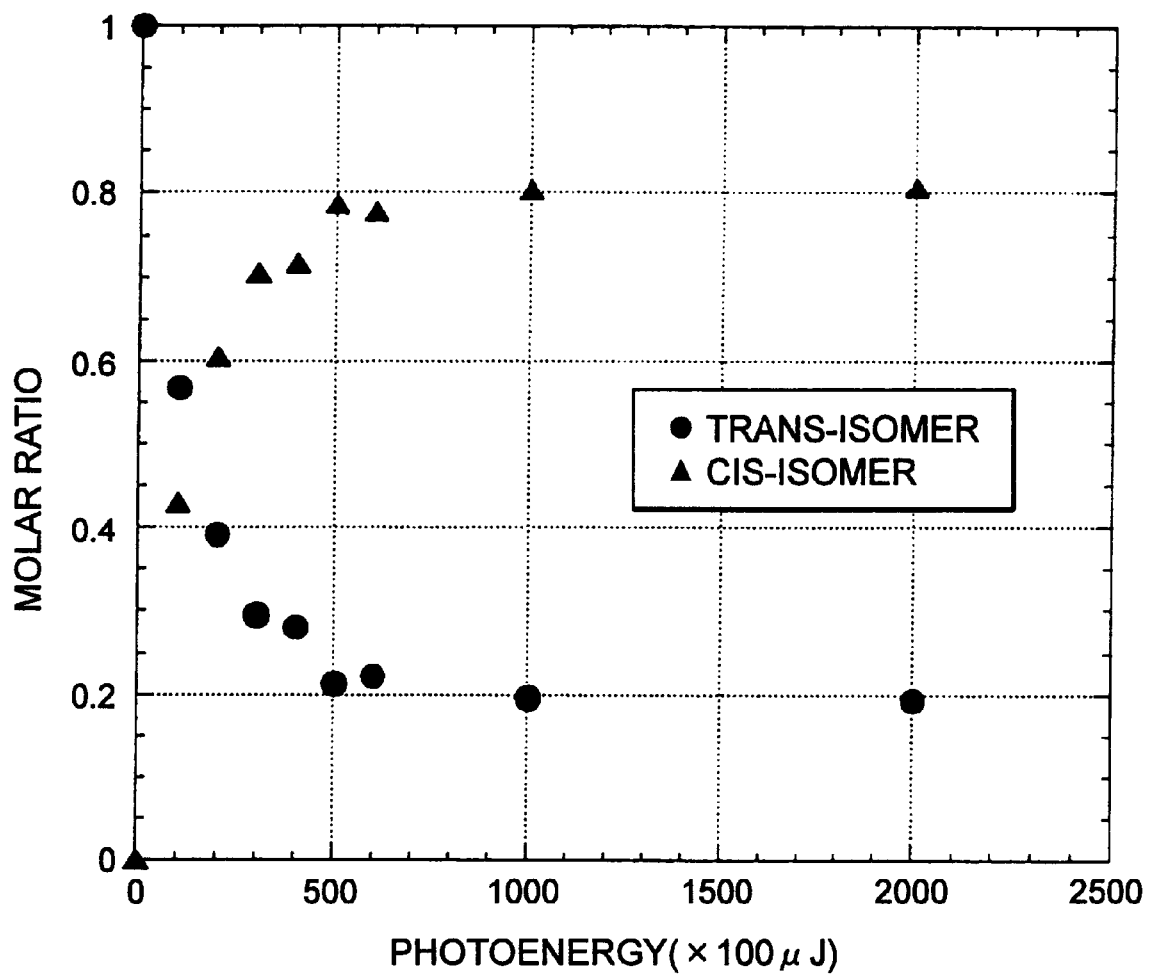
FIG. 2 is a graph showing the photoequilibrium between cis- and trans-isomers of 3-(2-β-D-galactopyranosyloxy-1-naphtyl)-2-propenic acid that is a substrate according to the invention.

As FIG. 2 shows, the ratio of the cis-isomer increased in proportion to the intensities of the irradiated light, and the ratio of cis-isomer to trans-isomer in terms of a molar ratio reached 1:4 under the equilibrium conditions.

Measurement (1) of Alkaline Phosphatase Activity

Employing trisodium=2-[1-(2-carboxylatoethenyl)] naphtylphosphite, the enzyme activity was measured. The irradiation conditions and enzyme reaction conditions are as follows:

Enzyme diluent buffer: 0.1 mol/l glycine-NaOH buffer (containing 1 mmol/l MgCl$_2$, 0.1 mmol/l ZnCl$_2$, and 0.25 g/l egg albumin; pH 9.5) Enzyme preparation: Alkaline phosphatase derived from calf small intestine (3.3 mg/ml, 2300 units/mg; Sigma Inc.) is diluted 1000-fold with the enzyme diluent as described above.

Substrate preparation: 0.1 mol/l glycine-NaOH buffer (pH 9.5) containing 0.4 mmol/l (0.14 g/l) sodium=2-[1-(2-carboxylatoethenyl)]naphtylphosphate Measurement Operations. The enzyme diluent buffer (1.95 ml) and the substrate preparation (1 ml) are charged into a 10×10 (mm) fluorescence cell and the cell is set in a fluorescence detector (under stirring with maintaining 30° C.). The enzyme diluent (0.05 ml) is added and the reaction is allowed to initiate under a room fluorescent lamp. The fluorescence intensity is measured at an excitation wavelength of 350 nm and a recording wavelength of 425 nm to detect the coumarin derivative formed.

Figure 3:
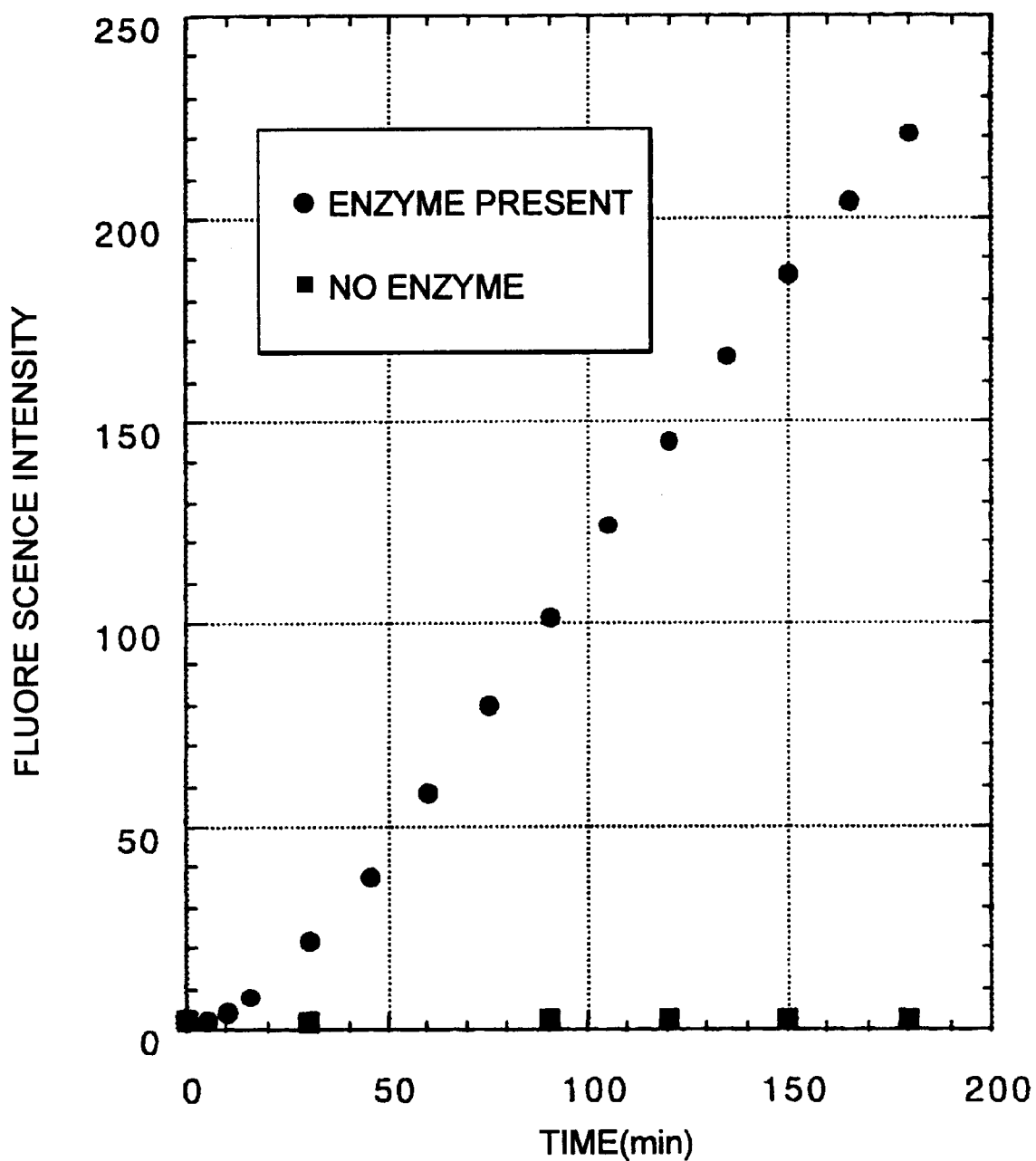
FIG. 3 is a graph showing the measurement of the activity of alkaline phosphatase using trisodium=2-[1(2-carboxylatoethenyl)]naphtylphosphite that is a substrate according to the invention.

FIG. 3 shows the time-dependence of fluorescence intensity as measured at 425 nm with an excitation wavelength of 350 nm in the presence of alkaline phosphatase where the solution containing only the substrate according to this invention was used as a control.

Measurement (2) of Alkaline Phosphatase Activity

Employing trisodium=[E] 2-[1-(2-carboxylatoethenyl)] naphtylphosphite, the enzyme activity was measured (nonirradiation conditions). The enzyme reaction conditions are as follows:

Enzyme diluent buffer: 0.1 mol/l glycine-NaOH buffer (containing 1 mmol/l MgCl$_2$, 0.1 mmol/l ZnCl$_2$, and 0.25 g/l egg albumin; pH 9.5)

Diluted enzyme preparation: Alkaline phosphatase derived from calf small intestine (3.3 mg/ml, 2300 units/mg; Sigma Inc.) is diluted 1000-fold with the enzyme diluent as described above.

Substrate preparation: 0.1 mol/l glycine-NaOH buffer (pH 9.5) containing trisodium=2-[1-(2-carboxylato ethenyl)] naphtylphosphate Quenching solution: 50 mmol/l citric acid-sodium citrate buffer (pH 4.0)

Figure 4:
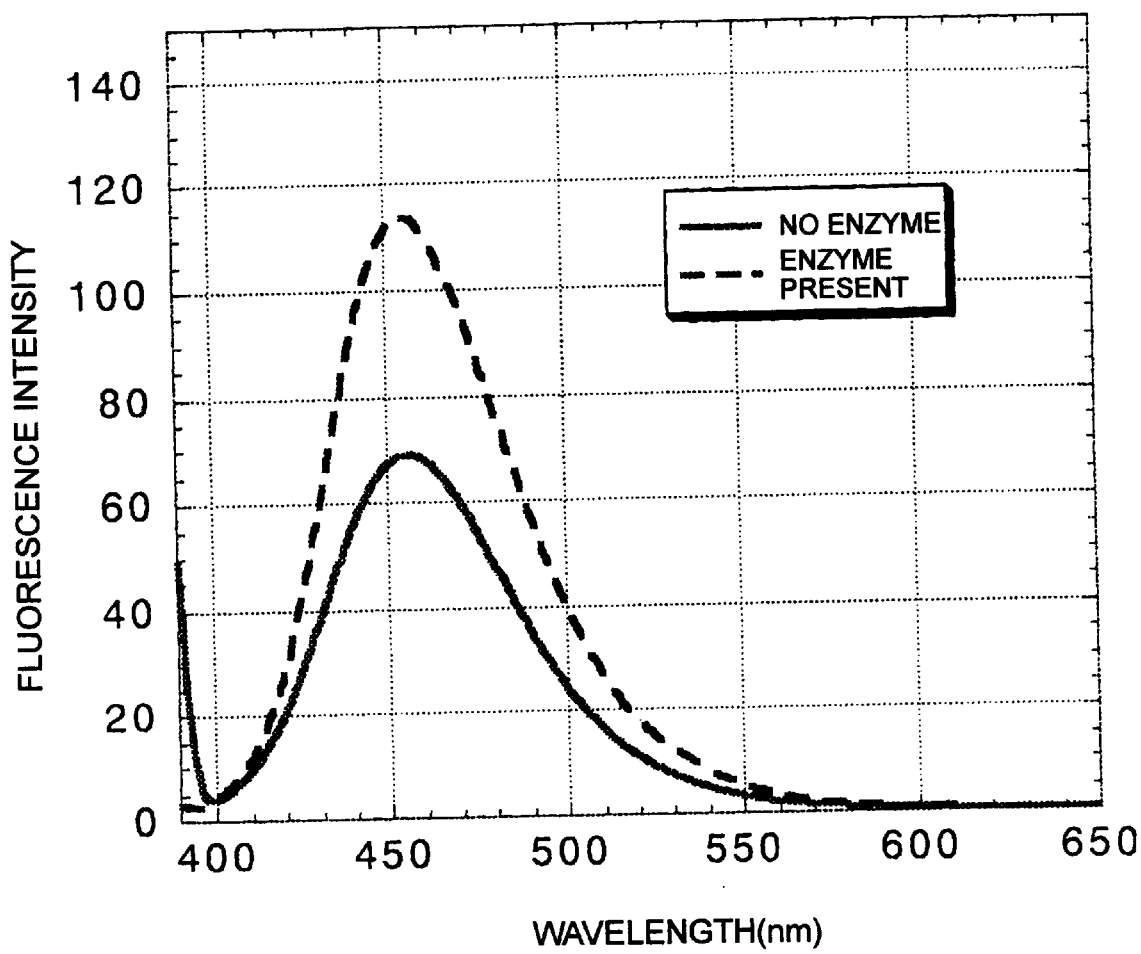
FIG. 4 is a graph showing the measurement of the activity of alkaline phosphatase using trisodium=(E)2-[1-(2-carboxylatoethenyl)]naphtylphosphite that is a substrate according to the invention.

Measurement Operations. The diluted enzyme preparation (100 μl) was allowed to stand at 30° C. for 5 min in a dark room, and to this was added 50 μl of the substrate preparation to initiate the enzyme reaction. The reaction was allowed to continue at 30° C. for 3 h. The quenching solution (2.5 ml) was added to terminate the enzyme reaction. The fluorescence intensity was then measured at an excitation wavelength of 350 nm and a recording wavelength of 425 nm by irradiation with UV light at 365 nm in 100 mJ. FIG. 4 shows a fluorescence spectrum at an excitation wavelength of 350 nm. The results in the absence of the enzyme are also shown together as a control.

Measurement (3) of Alkaline Phosphatase Activity

Moreover, the measurement of Km value for a substrate according to this invention against alkaline phosphatase was performed. The irradiation conditions and enzyme reaction conditions are as follows:

Enzyme diluent buffer: 0.1 mol/l glycine-NaOH buffer (containing 1 mmol/l $MgCl_2$ and 0.25 g bovine blood albumin; pH 9.5)

Enzyme preparation: Alkaline phosphatase derived from calf small intestine (3.3 mg/ml, 2300 units/mg; Sigma Inc.) is diluted 50-fold with the enzyme diluent as described above.

Substrate preparation: Glycine-NaOH buffer (0.1 mol/l, pH 9.5) containing five kinds of concentrations (0.3 mmol/l, 0.15 mmol/l, 0.12 mmol/l, 0.06 mmol/l, and 0.03 mmol/l) of sodium=2-[1-(2-carboxylatoethenyl)]naphtylphosphate is prepared.

Measurement Operations. The enzyme diluent buffer (1.95 ml) and the substrate preparation (1 ml) were charged into a 10×10 (mm) fluorescence cell and the temperature was maintained at 30° C. To this was added 0.05 ml of the enzyme diluent and it was allowed to react, while being stirred, for 30 min under a room fluorescent lamp. The fluorescence intensity was measured at an excitation wavelength of 350 nm and a recording wavelength of 425 nm.

Based on the results of measurements at the respective substrate concentrations thus obtained, the Km value was computed by making a Lineweaver-Burk plot, which resulted in 0.14 mM.

Measurement (4) of Alkaline Phosphatase Activity

Employing [E]2-[1-(2-carboxylatoethenyl)] 5-diethyl aminophenylphosphite, the enzyme activity was measured (nonirradiation conditions). The enzyme reaction conditions are as follows:

Enzyme diluent buffer: 0.1 mol/l glycine-NaOH buffer (containing 1 mmol/l $MgCl_2$, 0.1 mmol/l $ZnCl_2$, and 0.25 g/l egg albumin; pH 9.5)

Diluted enzyme preparation: Alkaline phosphatase derived from calf small intestine (3.3 mg/ml, 2300 units/mg; Sigma Inc.) is diluted 1000-fold with the enzyme diluent as described above.

Substrate preparation: 0.1 mol/l glycine-NaOH buffer (pH 9.5) containing (E)2-[1-(2-carboxylatoethenyl)] 5-diethylaminophenylphosphate Quenching solution: 50 mmol/l citric acid-sodium citrate buffer (pH 4.0)

Measurement Operations. The diluted enzyme preparation (100 μl) was allowed to stand at 30° C. for 5 min in a dark room, and to this was added 50 μl of the substrate preparation to initiate the enzyme reaction. The reaction was allowed to continue at 30° C. for 3 h. The quenching solution (2.5 ml) was added to terminate the enzyme reaction. The fluorescence intensity was then measured at an excitation wavelength of 360 nm and a recording wavelength of 460 nm by irradiation with UV light at 365 nm in 100 mJ. FIG. 4 shows a fluorescence spectrum illustrative of the results obtained. The results in the absence of the enzyme are also shown together as a control.

Measurement (1) of Acidic Phosphatase Activity

Employing trisodium=(E) 2-[1-(2-carboxylatoethenyl)] naphtylphosphite as a substrate, the measurement and computation of Km value for acidic phosphatase was performed. The irradiation conditions and enzyme reaction conditions are as follows:

Enzyme diluent buffer: 90 mmol/l citric acid buffer (pH 4.8)

Enzyme preparation: Acidic phosphatase derived from human prostate (0.5 mg, 23 units/mg; Sigma Inc.) is diluted to 1 ml with the enzyme diluent buffer as described above.

Substrate preparation: Citric acid buffer (90 mmol/l, pH 4.8) containing eight kinds of concentrations (1.0 mmol/l, 0.8 mmol/l, 0.6 mmol/l, 0.4 mmol/l, 0.2 mmol/l 0.1 mmol/l, 0.08 mmol/l, and 0.06 mmol/l) of sodium=2-[1-(2-carboxylatoethenyl)]-naphtylphosphate is prepared.

Measurement Operations. The enzyme diluent buffer (1 ml) and the substrate preparation (1 ml) are charged into a 10×10 (mm) fluorescence cell and the temperature is maintained at 37° C. To this is added 0.1 ml of the enzyme diluent and it is allowed to react for 30 min. After irradiation with light at 365 nm (500 $mJ/cm^2$), the fluorescence intensity was measured at an excitation wavelength of 350 nm and a recording wavelength of 425 nm.

Based on the results of measurements at the respective substrate concentrations thus obtained, the Km value was computed by making a Lineweaver-Burk plot, which resulted in 0.23 mM.

Figure 5:
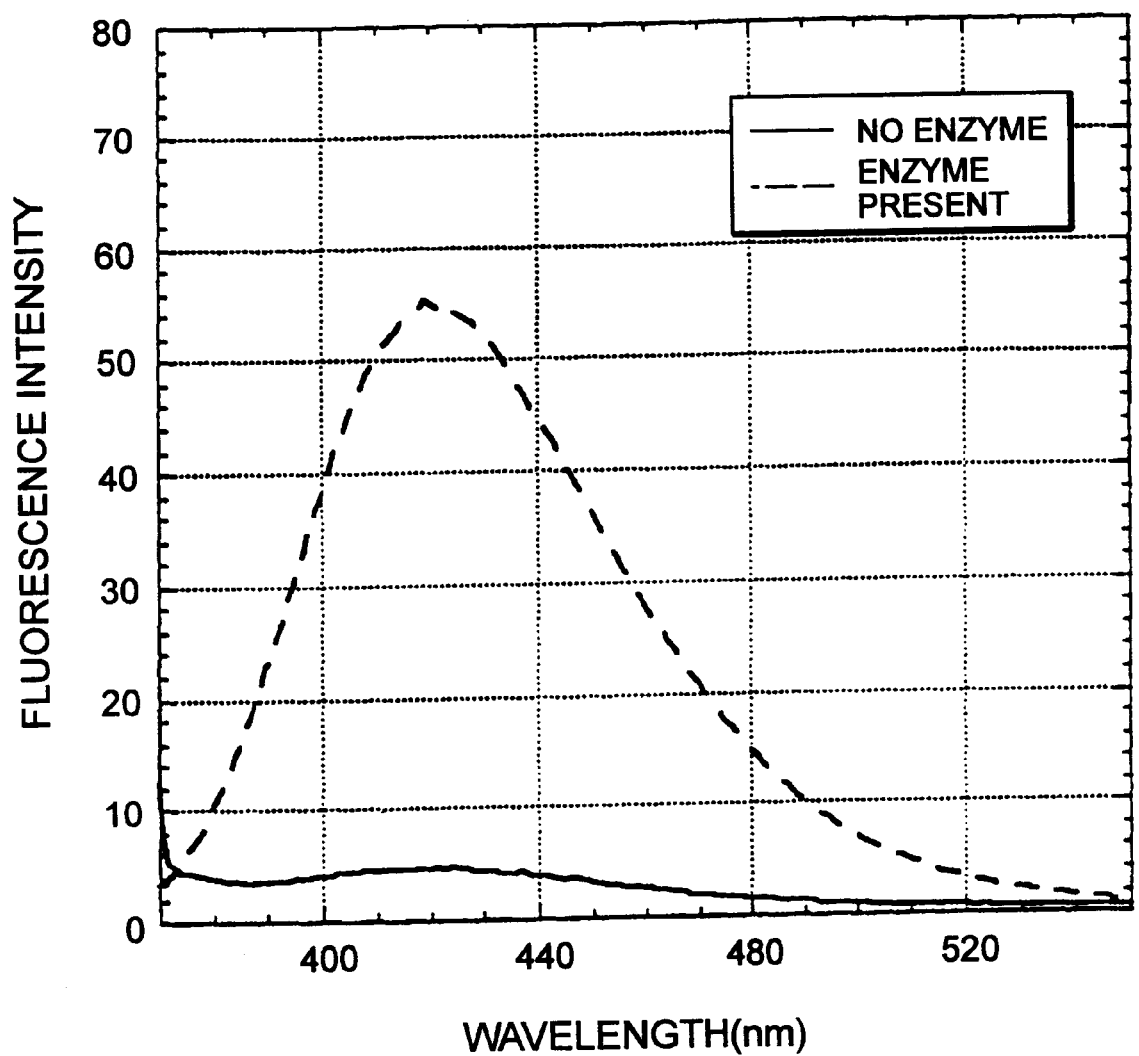
FIG. 5 is a graph showing the measurement of the activity of acidic phosphatase using trisodium=2-[1-(2-carboxylatoethenyl)]naphtylphosphite that is a substrate according to the invention.
Figure 6:
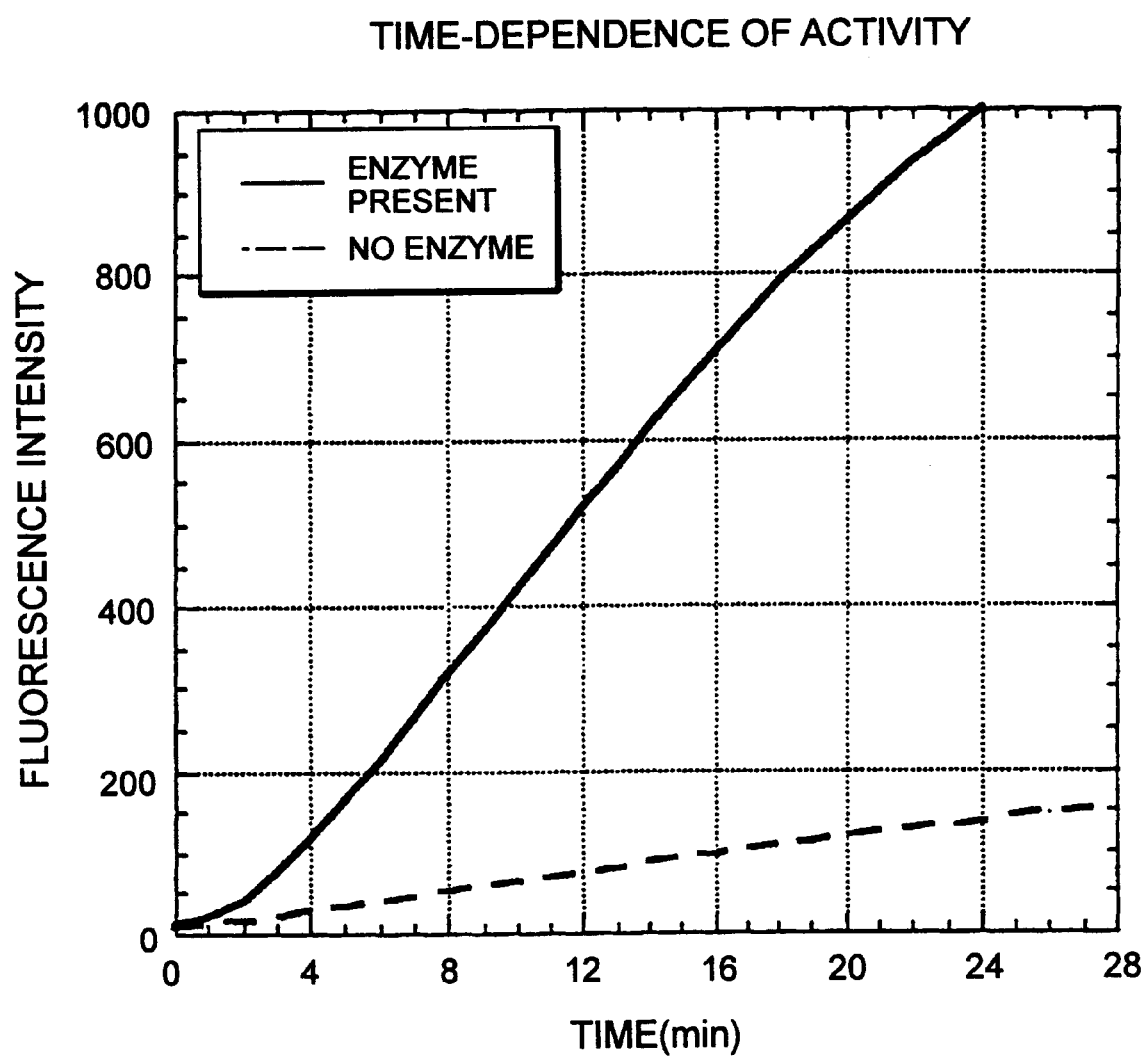
FIG. 6 is a graph showing the time-dependence of the activity of acidic phosphatase using trisodium=2-[1-(2-carboxylatoethenyl)]naphtylphosphite that is a substrate according to the invention.

FIG. 5 shows the fluorescence spectrum obtained as a result of the reaction between acidic phosphatase and the substrate, where the fluorescence due to a coumarin skeleton in the presence of the enzyme was observed. Furthermore, FIG. 6 shows the time-dependence of fluorescence intensity as measured at 425 nm with an excitation wavelength of 350 nm in the presence of acidic phosphatase, where the solution containing only the substrate according to this invention was used as a control.

Measurement (2) of Acidic Phosphatase Activity

Employing trisodium=2-(1-(2-carboxylatoethenyl)] naphtylphosphite (a mixture of E- and Z-isomers under irradiation conditions) as a substrate, the measurement and computation of Km value for acidic phosphatase was performed. The irradiatin conditions and enzyme reaction conditions are as follows:

Enzyme diluent buffer: 90 mmol/l citric acid buffer (pH 4.8)

Enzyme preparation: Acidic phosphatase derived from human prostate (0.5 mg, 23 units/mg; Sigma Inc.) is diluted to 1 ml with the enzyme diluent as described above.

Substrate preparation: Citric acid buffer (90 mmol/l, pH 4.8) containing eight kinds of concentrations (1.0 mmol/l, 0.8 mmol/l, 0.6 mmol/l, 0.4 mmol/l, 0.2 mmol/l 0.1 mmol/l, 0.08 mmol/l, and 0.06 mmol/l) of sodium=2-[1-(2-carboxylatoethenyl)]-naphtylphosphate is prepared.

Measurement Operations. The enzyme diluent buffer (1 ml) and the substrate preparation (1 ml) are charged into a 10×10 (mm) fluorescence cell and the temperature is maintained at 37° C. To this is added 0.1 ml of the enzyme preparation and it is allowed to react for 30 min. After irradiation with light at 365 nm (500 mJ/cm$^2$), the fluorescence intensity was measured at an excitation wavelength of 350 nm and a recording wavelength of 410 nm.

Based on the results of measurements at the respective substrate concentrations thus obtained, the Km value was computed by making a Lineweaver-Burk plot, which resulted in 1.5 mM Measurement of Galactosidase Activity In the Case of (E)3-[2-β-D-Galactopyranosyloxy-1-naphtyl)-2-propenic Acid Ethyl as a Substrate. Employing the substrate thus obtained above according to this invention, the enzyme reaction was carried out. The irradiation conditions and enzyme reaction conditions are as follows:

Enzyme diluent buffer: 10 mM phosphoric acid buffer (containing 0.1 mol/l NaCl, 1 mmol/l MgCl$_2$, and 0.03 g bovine blood albumin; pH 7.0)

Enzyme preparation: 6-D-Galactosidase derived from *E. coli* (50 mg/ml, 410 units/mg; Sigma Inc.) is diluted 100000-fold with the enzyme diluent buffer as described above.

Substrate preparation: 1 mol/l (E)3-[2-β-D-galacto pyranosyloxy-1-naphtyl)-2-propenic acid ethyl aqueous solution containing 2% dimethylformamide Measurement Operations. The enzyme preparation (2 ml) is charged into a 10×10 (mm) fluorescence cell and the temperature is maintained at 30° C. To this is added 1 ml of the substrate preparation and the reaction is allowed to initiate. After irradiation with light at 365 nm (500 mJ/cm$^2$), the fluorescence intensity is measured at an excitation wavelength of 350 nm and a recording wavelength of 410 nm.

Figure 7:
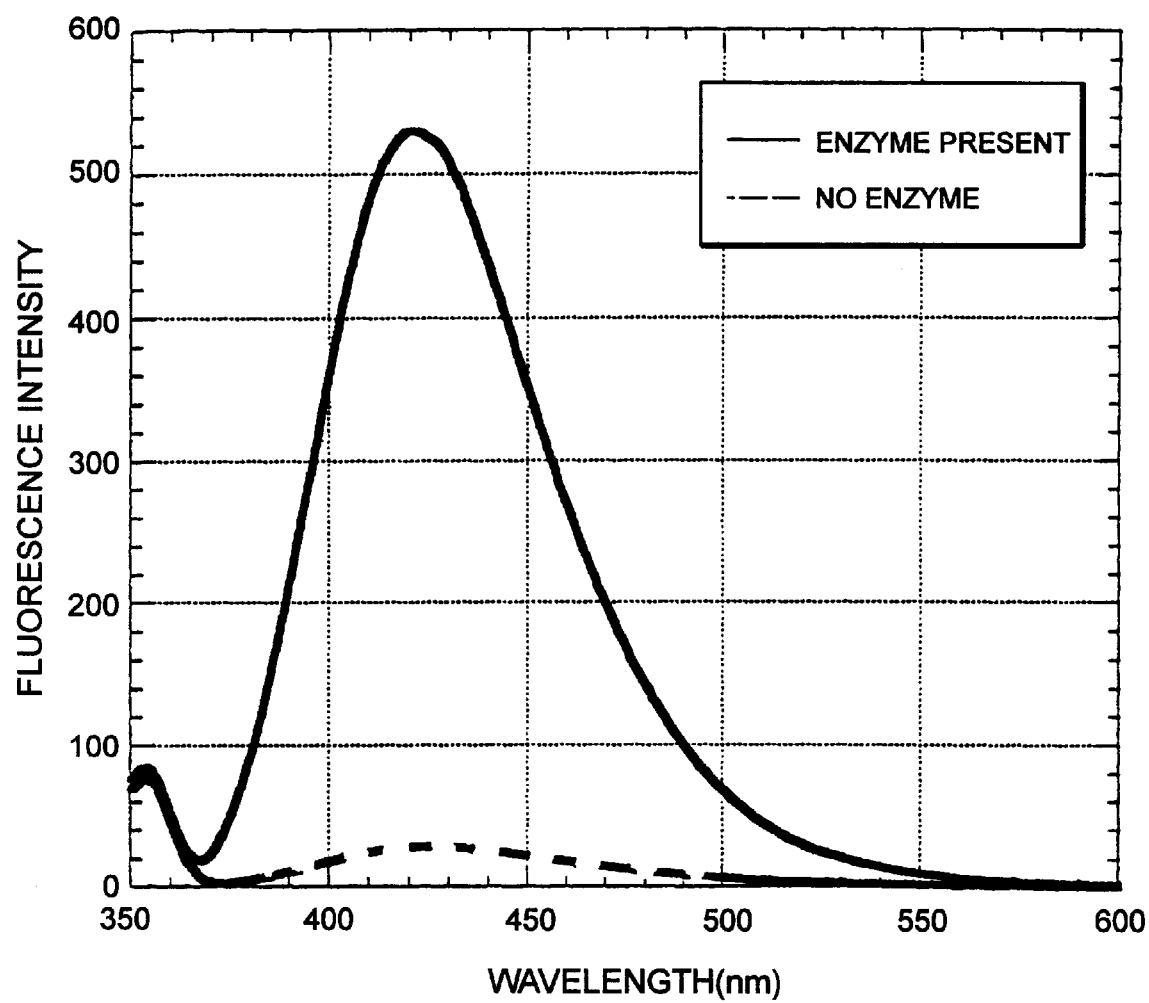
FIG. 7 is a graph showing the measurement of the activity of galactosidase using 3-(2-β-D-galactopyranosyloxy-1-naphtyl)-2-pronenoic acid ethyl ester that is a substrate according to the invention

FIG. 7 shows the fluorescence spectrum obtained as a result of the reaction between galactosidase and the substrate. The results in the absence of the enzyme are also shown together as a control.

Moreover, the measurement and computation of Km value for β-D-galactosidase, which was the substrate according to this invention, was performed. The required irradiation conditions and enzyme reaction conditions are as follows:

Enzyme diluent buffer: 10 mM phosphoric acid buffer (containing 0.1 mol/l NaCl, 1 mmol/l MgCl$_2$, and 0.03 g bovine blood albumin; pH 7.0)

Enzyme preparation: 6-Galactosidase derived from *E. coli* (50 mg/ml, 410 units/mg; Sigma Inc.) is diluted 100000-fold with the enzyme diluent buffer as described above.

Substrate preparation: Eight kinds of concentrations (0.4 mmol/l, 0.2 mmol/l, 0.15 mmol/l, 0.10 mmol/l, 0.08 mmol/l, 0.06 mmol/l, 0.05 mmol/l, 0.04 mmol, and 0.02 mmol/l) of (E) 3-[$^2$-,-D-galactopyranosyloxy-1-naphtyl)-2-propenic acid ethyl aqueous solution containing 2% dimethylformamide is prepared.

Measurement Operations. The enzyme diluent buffer (1 ml) and the substrate preparation (1 ml) are charged into a 10×10 (mm) fluorescence cell and the temperature is maintained at 37° C. To this is added 0.1 ml of the enzyme preparation and it is allowed to react for 30 min. After irradiation with light at 365 nm (500 mJ/cm$^2$), the fluorescence intensity was measured at an excitation wavelength of 350 nm and a recording wavelength of 410 nm.

Based on the results of measurements at the respective substrate concentrations thus obtained, the Km value was computed by making a Lineweaver-Burk plot, which resulted in 0.12 mM.

Performing operations similar to those described above on (E)-3-[2-β-D-galactopyranosyloxy-1-naphtyl)-2-propenic acid and (Z)-3-[2-β-D-galactopyranosyloxy-1-naphtyl)-2-propenic acid, respective Km values were also computed. Here, for (E)-3-[2-β-D-galactopyranosyloxy-1-naphtyl)-2-propenic acid, Km was 0.07 mM, while Km was 0.53 mM for (Z)-3-[2-β-D-galactopyranosyloxy-1-naphtyl)-2-propenic acid.

Measurement (1) of Esterase Activity

Employing 3(2-acetoxy-4-diethylaminophenyl)-2-propenic acid ethyl ester, the enzyme activity was measured. The irradiation and enzyme reaction conditions are as follows:

Enzyme diluent buffer: 100 mM phosphoric acid buffer (pH 8.0)

Enzyme preparation: Esterase derived from swine liver (210 units/mg; Sigma Inc.) is diluted to 10 mg/10 ml with the enzyme diluent buffer as described above.

Substrate preparation: 0.1 mmol/l (E)-3-(2-acetoxy-4-diethylaminophenyl)-2-propenic acid ethyl ester solution in acetone Quenching solution: ethanol/water 1:1

Figure 8:
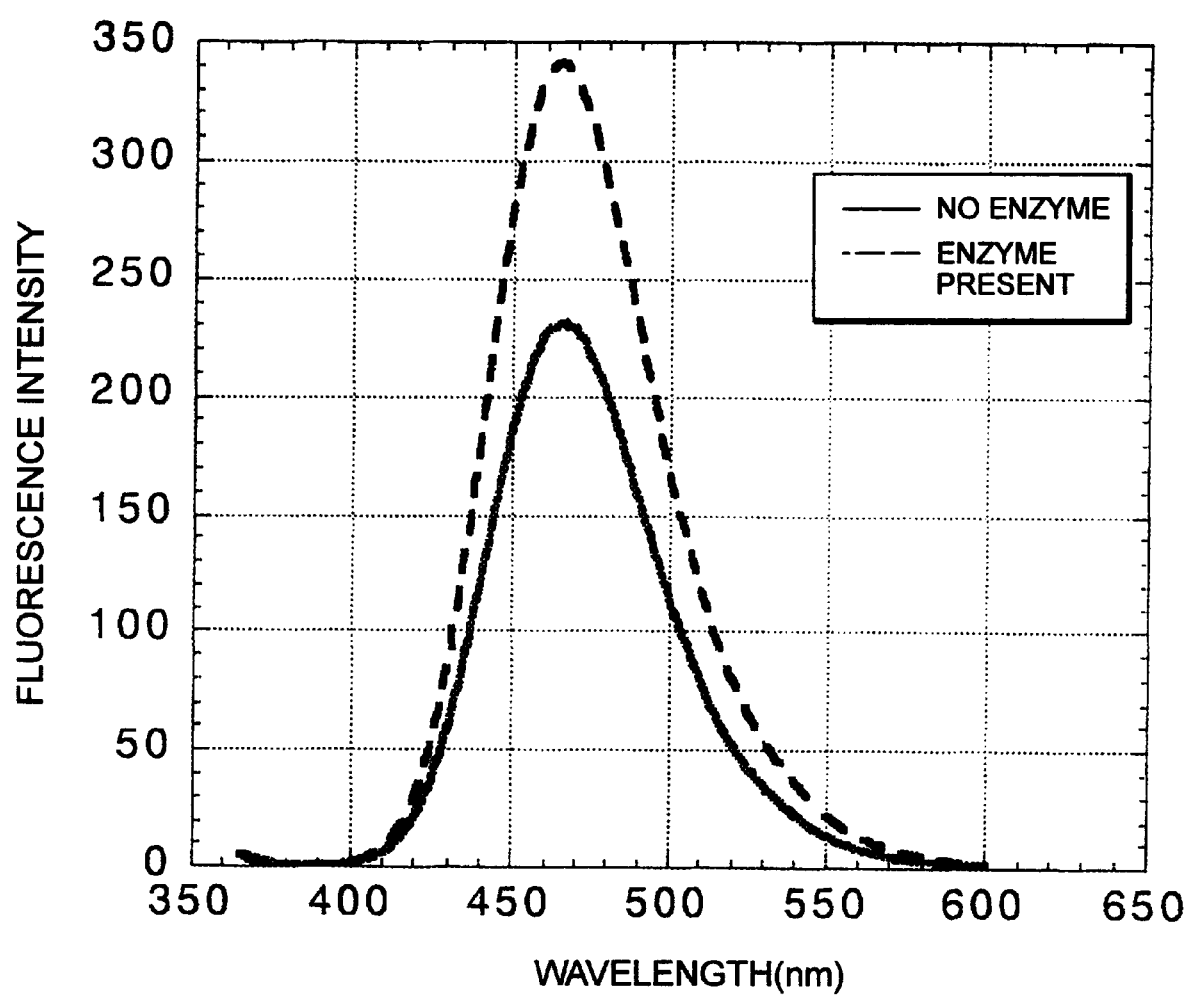
FIG. 8 is a graph showing the measurement of the activity of esterase using (E)-3-(2-acetoxy-4-diethylaminophenyl)-2-pronenoic acid ethyl ester that is a substrate according to the invention.

Measurement Operations. The diluted enzyme (100 μl) was allowed to stand in a dark room at 25° C. for 5 min, and to this was added 50 μl of the substrate preparation to initiate the enzyme reaction. The reaction was allowed to continue at 25° C. for 15 min. The quenching solution (2.5 ml) was added to terminate the enzyme reaction. The fluorescence intensity was then measured at an excitation wavelength of 360 nm and a recording wavelength of 460 nm by irradiation with UV light at 365 nm in 100 mJ. FIG. 8 shows the results obtained. The results in the absence of the enzyme are also shown together as a control.

Measurement (2) of Esterase Activity

Employing 3(2-acetoxy-4, 6-dimethoxyphenyl)-2-methyl 2-propenoic acid ethyl ester, the enzyme activity was measured. The irradiation and enzyme reaction conditions are as follows:

Enzyme diluent buffer: 100 mM phosphoric acid buffer (pH 8.0)

Enzyme preparation: Esterase derived from swine liver (210 units/mg; Sigma Inc.) is diluted to 10 mg/10 ml with the enzyme diluent buffer as described above.

Substrate preparation: 0.1 mmol/l (E)-3-(2-acetoxy-4,6-dimethoxylphenyl)-2-methyl-2-propenic acid ethyl ester solution in acetone Quenching solution: ethanol/water 1:1

Figure 9:
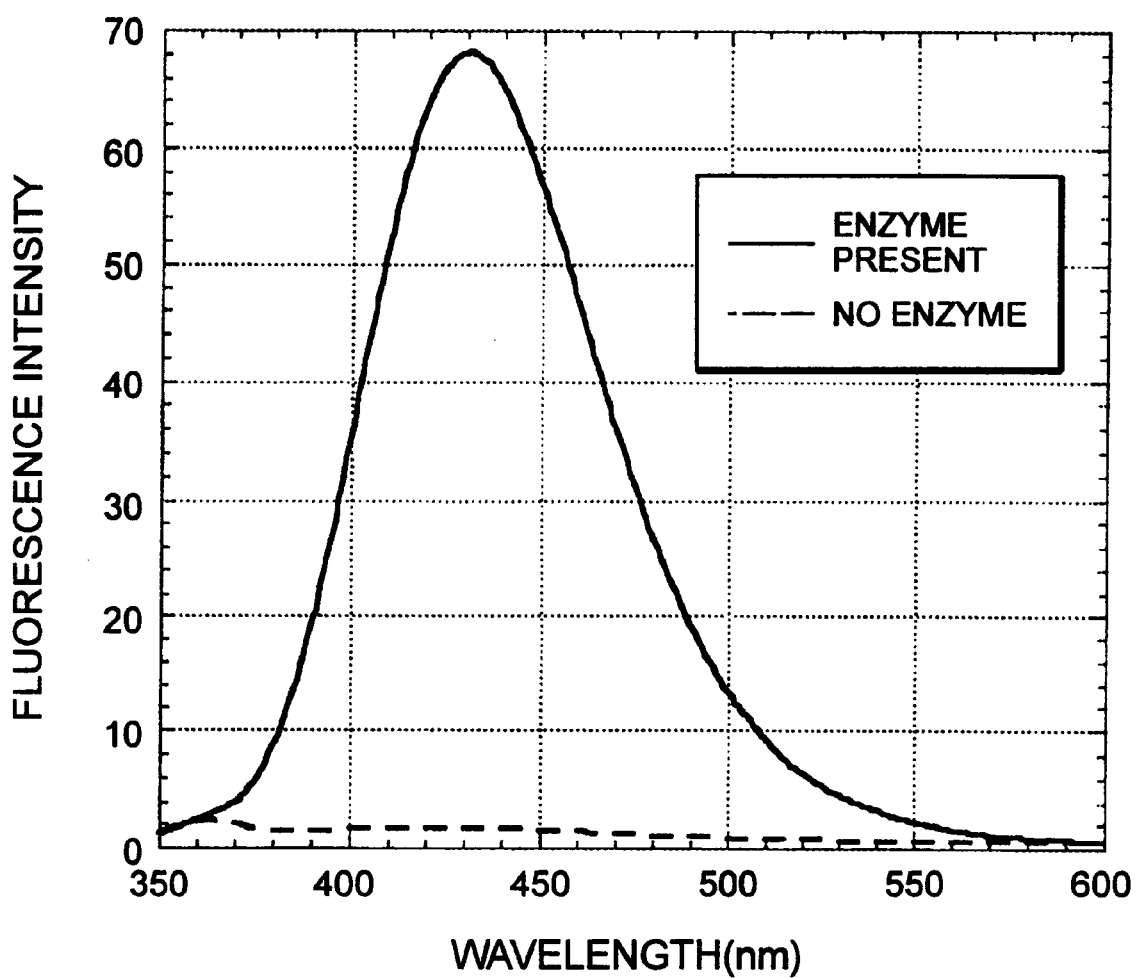
FIG. 9 is a graph showing the measurement of the activity of esterase using 3-(2-acetoxy-4,6-dimethoxyphenyl)-2-methyl-2-pronenoic acid ethyl ester that is a substrate according to the invention.

Measurement Operations. The diluted enzyme (100 μl) was allowed to stand in a dark room at 25° C. for 5 min, and to this was added 50 μl of the substrate preparation to initiate the enzyme reaction. The reaction was allowed to continue at 25° C. for 15 min. Subsequently, the quenching solution (2.5 ml) was added to terminate the enzyme reaction. The fluorescence intensity was then measured at an excitation wavelength of 325 nm and a recording wavelength of 430 nm after irradiation with UV light at 365 nm in 100 mJ. FIG. 9 shows the results obtained. The results in the absence of the enzyme are also shown together as a control.

Measurement (3) of Esterase Activity

Employing 3(2-acetoxy-1-naphtyl)-2-propenic acid ethyl ester, the enzyme activity was measured. The irradiation and enzyme reaction conditions are as follows:

Enzyme diluent buffer: 100 mM phosphoric acid buffer (pH 8.0)

Enzyme preparation: Esterase derived from swine liver (210 units/mg; Sigma Inc.) is diluted to 10 mg/10 ml with the enzyme diluent buffer as described above.

Substrate preparation: 0.1 mmol/l 3-(2-acetoxy-1-naphtyl)-2-propenic acid ethyl ester solution in acetone Quenching solution: ethanol/water 1:1

Figure 10:
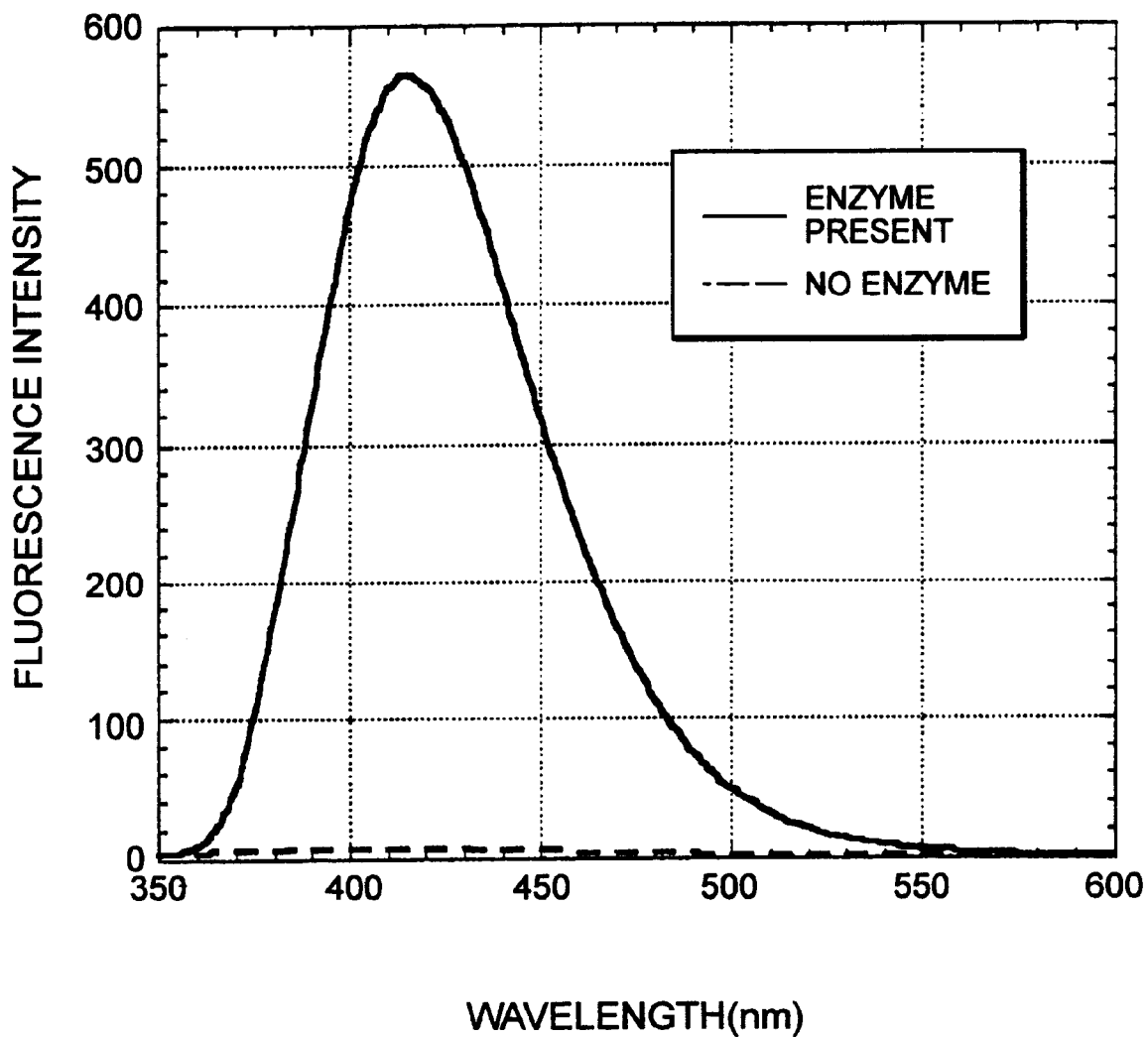
FIG. 10 is a graph showing the measurement of the activity of esterase using 3-(2-acetoxy-1-naphtyl)-2-pronenoic acid ethyl ester that is a substrate according to the invention.
Figure 11:
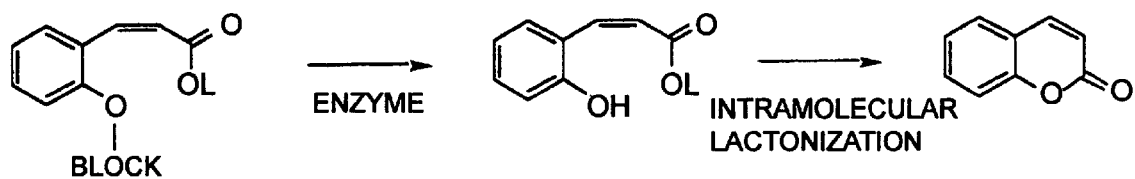
FIG. 11 is a graph showing the concept of the invention.

Measurement Operations. The diluted enzyme (100 μl) was allowed to stand in a dark room at 25° C. for 5 min, and to this was added 50 μl of the substrate preparation to initiate the enzyme reaction. The reaction was allowed to continue at 25° C. for 15 min. Subsequently, the quenching solution (2.5 ml) was added to terminate the enzyme reaction. The fluorescence intensity was then measured at an excitation wavelength of 325 nm and a recording wavelength of 425 nm after irradiation with UV light at 365 nm in 100 mJ. FIG. 10 shows the results obtained. The results in the absence of the enzyme are also shown together as a control.

INDUSTRIAL APPLICABILITY

The enzyme substrate according to this invention has within its molecule both a group to be cleaved by an enzyme reaction and a group that forms a strongly fluorescent coumarin derivative through intramolecular lactonization when cleaved by the enzyme reaction. Accordingly, when the enzyme reaction is conducted using such enzyme substrate, the coumarin derivative having no phenolic hydroxyl forms in the reaction solution as the enzyme reaction progresses. This allows the determination of enzyme activities without inhibiting the enzyme reaction through the consistent measurement of fluorescence of the coumarin derivative for a prolonged period. Thus, this invention has come to being applicable in enzyme immunoassays with high sensitivity.

We claim:

1. An enzyme substrate represented by the following formula:

(BLOCK-O)-$X_{cu}$ wherein BLOCK is a blocking group selected from the group consisting of:
a monovalent blocking group derivable by removal of one hydroxyl from a phosphoric acid group, a sulfuric acid group, or a salt thereof; and a monovalent blocking group derivable by removal of a hydroxyl from an aliphatic carboxyl, an aromatic carboxyl, an amino acid carboxyl, or a peptide carboxyl, wherein said BLOCK is cleaved from said substrate by the action of an enzyme to yield a HO—$X_{cu}$ product, and further, said HO—$X_{cu}$ product intramolecularly forms a lactone ring to provide a coumarin derivative;

wherein $X_{cu}$ has a structure represented by the following formula and is covalently bound to oxygen O at $C^1$ carbon,

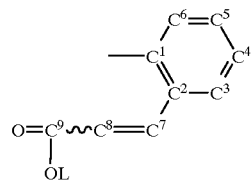

wherein L represents H, NH, alkyl having 1 to 4 carbons, tetralkylammonium having 1 to 4 carbons, or an alkaline metal or an alkaline earth metal; and further, wherein said coumarin derivative has a structure represented by the following formula:

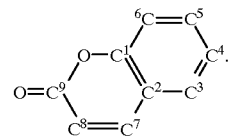

2. The enzyme substrate according to claim 1, wherein the $C^3$–$C^4$ bond forms a 5- or 6-membered aromatic ring; H is bound to $C^5$, $C^6$, and $C^7$; and H or $CH_3$ is bound to $C^8$.

3. The enzyme substrate according to claim 2, wherein the X, has a structure represented by the following formula:

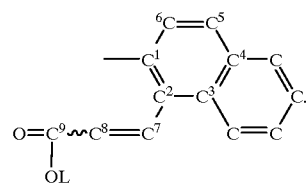

4. The enzyme substrate according to claim 1, wherein dialkylamino having 1 to 3 carbons is bound to $C^5$; hydrogen is bound to $C^3$, $C^4$, $C^6$, and $C^7$; and H or $CH_3$ is bound to $C^8$.

5. The enzyme substrate according to claim 4, wherein X, has a structure represented by the following formula:

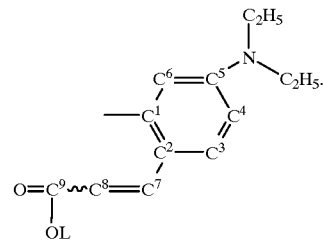

6. The enzyme substrate according to claim 1, wherein alkoxy having 1 to 3 carbons is bound to $C^3$ and $C^5$; H is bound to $C^4$, $C^6$, and $C^7$; and H or $CH^3$ is bound to $C^8$.

7. The enzyme substrate according to claim 6, wherein the $X_{cu}$ has a structure represented by the following formula:

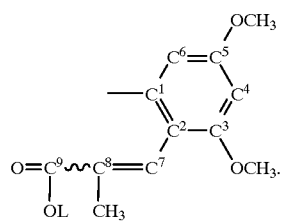

8. The enzyme substrate according to claim 1, wherein the BLOCK is a phosphoric acid group ($PO_3^-$).

9. The enzyme substrate according to claim 1, wherein the BLOCK is acetyl ($CH_3CO$).

10. A method for detecting an enzyme activity, said method comprising the steps of:

(A) contacting a sample containing an enzyme having an activity to be detected, with an enzyme substrate represented by the following formula:

(BLOCK-O)-$X_{cu}$ wherein BLOCK is a blocking group selected from the group consisting of:
a monovalent blocking group derivable by removal of one hydroxyl from a phosphoric acid group, a sulfuric acid group, or a salt thereof; and a monovalent blocking group derivable by removal of a hydroxyl from an aliphatic carboxyl, an aromatic carboxyl, an amino acid carboxyl, or a peptide carboxyl, wherein said BLOCK is cleaved from said substrate by the action of an enzyme to yield a HO—$X_{cu}$ product, and further, said HO—$X_{cu}$ product intramolecularly forms a lactone ring to provide a coumarin derivative;

wherein $X_{cu}$ has a structure represented by the following formula, the $C^7$–$C^2$ bond and the $C^8$–$C^9$ bond have cis-configuration with respect to the $C^7$=$C^8$ double bond, and the $X_{cu}$ is covalently bound to oxygen O at the $C^1$ carbon,

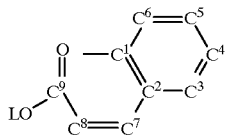

wherein L represents H, NH, alkyl having 1 to 4 carbons, tetralkylammonium having 1 to 4 carbons, or an alkaline metal or an alkaline earth metal; and further, wherein said coumarin derivative has a structure represented by the following formula:

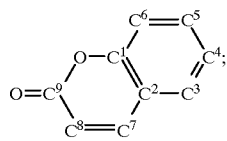

(B) detecting said coumarin derivative, and correlating the detected coumarin derivative to detect the enzyme activity.

11. A method for detecting an enzyme activity, said method comprising the steps of:

(A) contacting a sample containing an enzyme having an activity to be detected, under irradiation conditions, with an enzyme substrate represented by the following formula:

(BLOCK-O)-$X_{cu}$ wherein BLOCK is a blocking group selected from the group consisting of:
a monovalent blocking group derivable by removal of one hydroxyl from a phosphoric acid group, a sulfuric acid group, or a salt thereof; and a monovalent blocking group derivable by removal of a hydroxyl from an aliphatic carboxyl, an aromatic carboxyl, an amino acid carboxyl, or a peptide carboxyl, wherein said BLOCK is cleaved from said substrate by the action of an enzyme to yield a HO—$X_{cu}$ product, and further, said HO—$X_{cu}$ product intramolecularly forms a lactone ring to provide a coumarin derivative;

wherein $X_{cu}$ has a structure represented by the following formula, the $C^7$–$C^2$ bond and the $C^8$–$C^9$ bond have trans-configuration with respect to the $C^7$=$C^8$ double bond, and the $X_{cu}$ is covalently bound to oxygen O at the $C^1$ carbon,

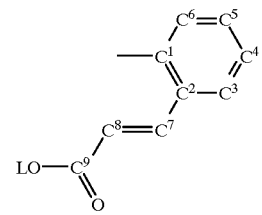

wherein L represents H, NH, alkyl having 1 to 4 carbons, tetralkylammonium having 1 to 4 carbons, or an alkaline metal or an alkaline earth metal; and further, wherein said coumarin derivative has a structure represented by the following formula:

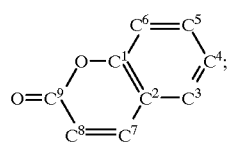

(B) detecting said coumarin derivative, and correlating the detected coumarin derivative to detect the enzyme activity.

12. The method according to claim 10, wherein the $X_{cu}$ is a substrate in which the $C^3$–$C^4$ bond forms a 5- or 6-membered aromatic ring; H is bound to $C^5$, $C^6$; and $C^7$, and H or $CH_3$ is bound to $C^8$.

13. The method according to claim 12, wherein $X_{cu}$ is a substrate having a structure represented by the following formula:

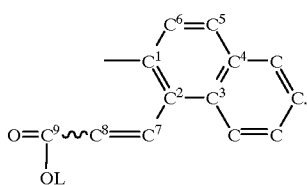

14. The method according to claim 10, wherein $X_{cu}$ is a substrate in which dialkylamino having 1 to 3 carbons is bound to $C^5$; hydrogen is bound to $C^3$, $C^4$, $C^6$, and $C^7$; and H or a $CH_3$ group is bound to $C^8$.

15. The method according to claim 14, wherein the $X_{cu}$ is a substrate having a structure represented by the following formula:

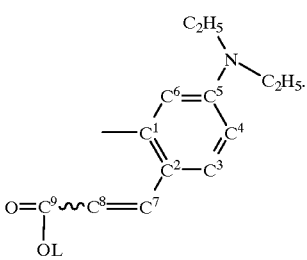

16. The method according to claim 10, wherein the $X_{cu}$ is a substrate in which alkyloxy having 1 to 3 carbons is bound to $C^3$ and $C^5$; H is bound to $C^4$, $C^6$, and $C^7$; and H or $CH_3$ is bound to $C^8$.

17. The method according to claim 16, wherein the $X_{cu}$ is a substrate having a structure represented by the following formula:

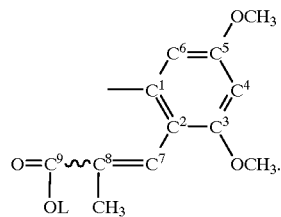

18. The method according to claim 10, wherein the step of detecting the coumarin derivative is to detect the fluorescence of the coumarin derivative.

19. The method according to claim 10, wherein
the BLOCK is a phosphoric acid group ($PO_3^-$) and said method is to determine the activity of alkaline phosphatase.

20. The method according to claim 10, wherein the BLOCK is a phosphoric acid group ($PO_3^-$) and said method is to determine the activity of acidic phosphatase.

21. The method according to claim 10, wherein the BLOCK is acetyl ($CH_3CO$) and said method is to determine the activity of esterase.

* * * * *